(12) United States Patent
Busch et al.

(10) Patent No.: US 12,053,901 B2
(45) Date of Patent: *Aug. 6, 2024

(54) COMPLIANT ANVIL

(71) Applicant: The Procter & Gamble Company, Cincinnati, OH (US)

(72) Inventors: James William Busch, Maineville, OH (US); Chad Burnett, Cincinnati, OH (US); Jennifer Lynn Schallick, Guilford, IN (US); Stephen Douglas Congleton, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/835,108

(22) Filed: Jun. 8, 2022

(65) Prior Publication Data

US 2022/0297337 A1 Sep. 22, 2022

Related U.S. Application Data

(63) Continuation of application No. 16/700,020, filed on Dec. 2, 2019, now Pat. No. 11,389,986.

(Continued)

(51) Int. Cl.
| | |
|---|---|
| *B26F 1/42* | (2006.01) |
| *B26F 1/38* | (2006.01) |
| *B26F 1/44* | (2006.01) |
| *B29C 55/18* | (2006.01) |
| *B26F 1/40* | (2006.01) |

(52) U.S. Cl.
CPC ............... *B26F 1/42* (2013.01); *B26F 1/384* (2013.01); *B26F 1/44* (2013.01); *B29C 55/18* (2013.01); *B26F 2001/402* (2013.01); *B26F 2001/4409* (2013.01)

(58) Field of Classification Search
CPC .... B26F 1/42; B26F 1/384; B26F 1/44; B26F 2001/402; B29C 55/18
USPC ........ 83/698.31, 698.42, 331–335, 659, 663, 83/346–347, 667, 339, 698, 911, 510; 492/56; 162/204
See application file for complete search history.

(56) References Cited

U.S. PATENT DOCUMENTS

| | | | | |
|---|---|---|---|---|
| 844,171 | A * | 2/1907 | McAnulty | B26D 7/2628 83/698.61 |
| 1,040,012 | A * | 10/1912 | Raabe | B65H 5/062 271/274 |

(Continued)

FOREIGN PATENT DOCUMENTS

| | | | | |
|---|---|---|---|---|
| WO | WO-2005087993 A1 * | 9/2005 | | D01G 1/04 |
| WO | 2010119022 | 10/2010 | | |

OTHER PUBLICATIONS

All Office Actions; U.S. Appl. No. 16/700,020.
Extended European Search Report and Search Opinion; Application No. 19213061.5; dated May 6, 2020; 9 pages.

*Primary Examiner* — Nhat Chieu Q Do
(74) *Attorney, Agent, or Firm* — Sarah M. DeCristofaro; William E. Gallagher

(57) ABSTRACT

An anvil roll is configured to operatively engage with a tooling agent. The anvil includes an outer surface, an opposing surface opposite the outer surface and an inner surface. One or more spring elements are disposed between the opposing surface and the inner surface. The springs provide a compliance to the anvil.

4 Claims, 11 Drawing Sheets

Related U.S. Application Data

(60) Provisional application No. 62/776,043, filed on Dec. 6, 2018.

(56) References Cited

U.S. PATENT DOCUMENTS

| | | | |
|---|---|---|---|
| 1,553,352 A * | 9/1925 | Amidon | C14B 1/56 101/22 |
| 2,585,410 A * | 2/1952 | Schott | B44B 5/026 492/42 |
| 2,953,291 A * | 9/1960 | Huck | B65H 35/08 226/153 |
| 4,004,479 A * | 1/1977 | Bodnar | B23D 33/02 83/345 |
| 4,765,604 A | 8/1988 | Trogan | |
| 4,856,400 A * | 8/1989 | Kelzer | B26D 3/085 83/885 |
| 5,167,897 A | 12/1992 | Weber et al. | |
| 5,257,965 A * | 11/1993 | Fuchs | D21G 1/0213 492/42 |
| 5,360,420 A | 11/1994 | Cook et al. | |
| 5,599,335 A | 2/1997 | Goldman et al. | |
| 5,628,097 A | 5/1997 | Benson | |
| 5,643,588 A | 7/1997 | Roe | |
| 5,674,216 A | 10/1997 | Buell et al. | |
| 5,702,551 A | 12/1997 | Huber et al. | |
| D409,343 S | 5/1999 | Kingry et al. | |
| 5,968,025 A | 10/1999 | Roe | |
| 6,003,191 A | 12/1999 | Sherry et al. | |
| D423,742 S | 4/2000 | Kingry et al. | |
| 6,107,537 A | 8/2000 | Elder | |
| 6,118,041 A | 9/2000 | Roe et al. | |
| 6,120,487 A | 9/2000 | Ashton | |
| 6,153,209 A | 11/2000 | Vega et al. | |
| 6,166,117 A | 12/2000 | Miyazaki | |
| 6,305,046 B1 | 10/2001 | Kingry et al. | |
| 6,410,129 B2 | 6/2002 | Zhang | |
| 6,426,444 B2 | 7/2002 | Roe et al. | |
| 6,484,346 B2 | 11/2002 | Kingry et al. | |
| 6,561,354 B1 | 5/2003 | Fereshtehkhou et al. | |
| 6,586,652 B1 | 7/2003 | Roe et al. | |
| 6,601,261 B1 | 8/2003 | Holt et al. | |
| 6,617,016 B2 | 9/2003 | Zhang et al. | |
| 6,627,787 B1 | 9/2003 | Roe et al. | |
| 6,645,190 B1 | 11/2003 | Olson et al. | |
| 6,645,604 B1 | 11/2003 | Fereshtehkhou et al. | |
| 6,647,849 B2 | 11/2003 | Jones | |
| 6,651,290 B2 | 11/2003 | Kingry et al. | |
| D489,537 S | 5/2004 | Wong et al. | |
| 6,761,711 B1 | 7/2004 | Fletcher et al. | |
| 6,777,064 B1 | 8/2004 | Brown et al. | |
| 6,787,512 B1 | 9/2004 | Verrall et al. | |
| 6,790,794 B2 | 9/2004 | Fereshtehkhou et al. | |
| 6,797,357 B2 | 9/2004 | Fereshtehkhou et al. | |
| D498,930 S | 11/2004 | Wong et al. | |
| 6,813,801 B2 | 11/2004 | Tanaka | |
| 6,817,994 B2 | 11/2004 | Popp et al. | |
| 6,825,393 B2 | 11/2004 | Roe et al. | |
| D499,887 S | 12/2004 | Wong et al. | |
| 6,840,928 B2 | 1/2005 | Datta et al. | |
| D501,609 S | 2/2005 | Wong et al. | |
| 6,849,067 B2 | 2/2005 | Fletcher et al. | |
| 6,861,571 B1 | 3/2005 | Roe et al. | |
| 6,893,426 B1 | 5/2005 | Popp et al. | |
| 6,936,330 B2 | 8/2005 | Fereshtehkhou et al. | |
| 6,953,452 B2 | 10/2005 | Popp et al. | |
| D511,251 S | 11/2005 | Wong | |
| 6,969,377 B2 | 11/2005 | Koele et al. | |
| 7,156,833 B2 | 1/2007 | Couture-Dorschner et al. | |
| 7,201,744 B2 | 4/2007 | Van Gompel et al. | |
| 7,219,386 B2 | 5/2007 | Tsuchiya et al. | |
| 7,293,317 B2 | 11/2007 | Tsuchiya et al. | |
| 7,383,602 B2 | 6/2008 | Tanaka et al. | |
| 7,497,851 B2 | 3/2009 | Koele et al. | |
| 7,682,349 B2 | 3/2010 | Popp et al. | |
| D615,378 S | 5/2010 | Koenig | |
| 7,803,726 B2 | 9/2010 | Policicchio et al. | |
| 7,862,550 B2 | 1/2011 | Koele et al. | |
| 7,901,393 B2 | 3/2011 | Matsuda et al. | |
| 8,007,485 B2 | 8/2011 | Popp et al. | |
| 8,361,048 B2 | 1/2013 | Kuen et al. | |
| 8,372,052 B2 | 2/2013 | Popp et al. | |
| 8,578,564 B2 | 11/2013 | Policicchio | |
| 8,579,876 B2 | 11/2013 | Popp et al. | |
| 8,747,379 B2 | 6/2014 | Fletcher et al. | |
| 8,756,746 B2 | 6/2014 | Policicchio | |
| 8,763,197 B2 | 7/2014 | Policicchio | |
| 8,931,132 B2 | 1/2015 | Policicchio | |
| 9,421,137 B2 | 8/2016 | Lavon | |
| 9,498,389 B2 | 11/2016 | Trennepohl | |
| 2006/0213801 A1 | 9/2006 | Karaoren et al. | |
| 2010/0233438 A1 | 9/2010 | Stone et al. | |
| 2010/0233439 A1 | 9/2010 | Stone et al. | |
| 2011/0186468 A1 | 8/2011 | Denome et al. | |
| 2011/0188784 A1 | 8/2011 | Denome et al. | |
| 2013/0211363 A1 | 8/2013 | LaVon et al. | |
| 2014/0005020 A1 | 1/2014 | Lavon et al. | |
| 2014/0041493 A1 | 2/2014 | Dulaney | |
| 2014/0097569 A1 | 4/2014 | Sposato, Jr. et al. | |
| 2016/0136014 A1 | 5/2016 | Arora | |
| 2017/0174387 A1 | 6/2017 | Johansson et al. | |
| 2018/0154533 A1 | 6/2018 | Busch | |
| 2018/0207830 A1 | 7/2018 | Borges Fernandez et al. | |
| 2019/0176450 A1 | 6/2019 | Busch | |
| 2020/0180182 A1 | 6/2020 | Busch et al. | |

\* cited by examiner

COMPLIANT ANVIL

CROSS REFERENCE TO RELATED APPLICATIONS

This application is a continuation application of U.S. application Ser. No. 16/700,020, filed on Dec. 2, 2019, and issued as U.S. Pat. No. 11,389,986, which claims the benefit of U.S. Provisional Application No. 62/776,043, filed on Dec. 6, 2018, the entireties of which are all incorporated by reference herein.

FIELD OF THE INVENTION

The present disclosure relates to apparatuses and methods for manufacturing articles such as absorbent articles and sanitary tissue products or components of such articles. More particularly, the present disclosure relates to apparatuses and methods involving anvil rolls such as bonding, cutting and the like.

BACKGROUND OF THE INVENTION

Along an assembly line, various types of articles, for example sanitary napkins, diapers, bath tissue, paper toweling, and facial tissues, may be produced by adding components to and/or otherwise modifying an advancing, continuous web of material. For example, webs or components may be bonded, embossed, cut, printed or otherwise modified while being advanced. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Webs of material and component parts used to manufacture sanitary napkins may include: backsheets, topsheets, secondary topsheets, absorbent core components, release paper wrappers, and the like.

Often, webs are passed through a nip formed between a tool and an anvil, one or both of which may be in the form of a cylindrical roll and rotate about an axis. To perform the desired operation, the tool operatively engages with the anvil through contact, interference or other known processes. The interaction between the two mechanisms results in deformation and wear. For instance, in cutting operations, there may be interference between the knife and the anvil which causes deformation of the knife. Indeed, in certain rotary cutting operations, a knife tool and anvil are set so close to one another that the knife must slightly deform to permit the tooling roll and anvil to continue to counter rotate. For example, the knife may have a height of 40 mm and the peripheral surfaces of the tooling roll and anvil may be set such that they are only 39.9 mm apart. Thus, when a web is fed through the nip, deformation of movement of 0.1 mm must be provided to permit the knife to pass through the nip between the rotating surfaces. This causes localized, and often multidirectional, deformation of the knife. This can lead to rapid degradation of the cutting surface of the knife and material fatigue of the entire knife, necessitating repair or replacement. Moreover, shards from the knife may migrate into the web causing safety hazards. These risks are heightened when the cutting operation involves a curvilinear knife.

In addition, there is often a very small process window for effective performance. That is, very little variance in process conditions is acceptable. For instance, when bonding substrates, operating parameters such as the distance between the bonding surface and anvil, the thickness of the substrates to be bonded, and the pressure that may be exerted on the substrate by a pressure applying member, must be maintained within relatively tight tolerances to prevent premature failure of the apparatus and/or defects in the substrate. When the pressure applying member and the anvil are rigid, engagement for too long or too short of time, at the wrong location, where the substrates are too thick or thin, at the wrong pressure and/or at the wrong angle can lead to damage to equipment, failed or ineffective bonds, and/or tearing of the substrates. As a result, converting processes currently require a large degree of setup in order to work within the narrow process windows.

Therefore, there is a continued need for a method and apparatus that effectively modifies webs while permitting more freedom for process variability. There is also a need for a method and apparatus that reduces the likelihood of defects in the web. In addition, there is a need to enhance manufacturing efficiency and reduce costs, such as costs for maintenance and replacement of parts.

DETAILED DESCRIPTION OF EXAMPLES

Definitions

Figure 1:
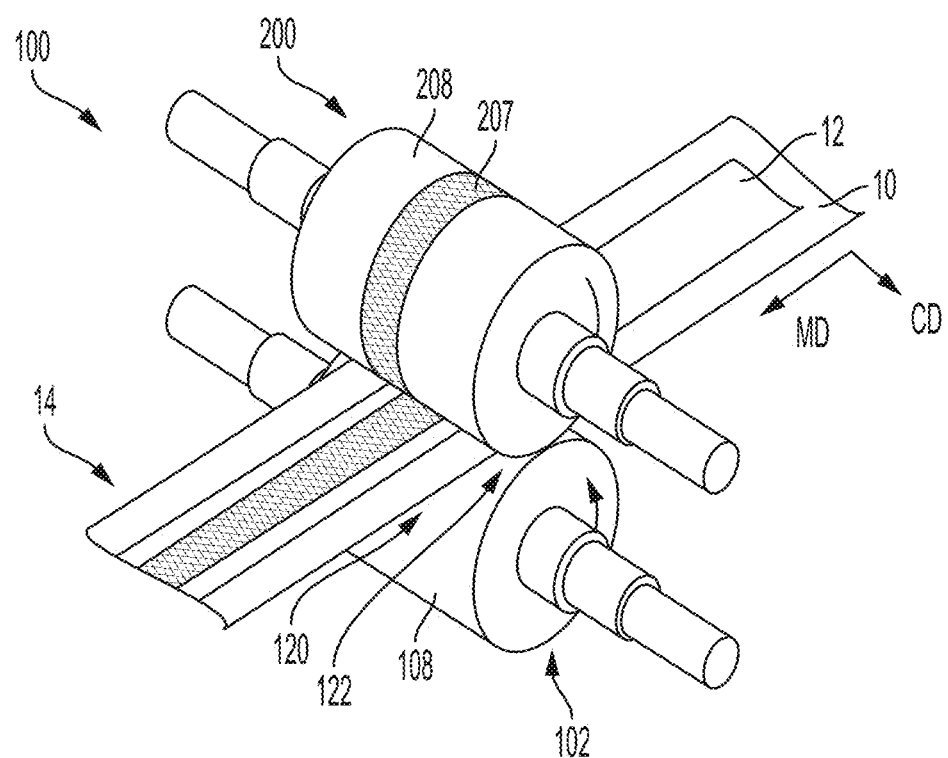
FIG. 1 is a perspective view of an apparatus.

"Compliance" or "compliance value" as used herein refers to a displacement vector; a displacement vector being distance and direction that a component is deformed from its equilibrium length. The displacement vector of a spring is expressed as x in the equation $F=-kx$, when the spring operates according to Hooke's Law, or x in the equation $F=k*f(x)$ when the spring does not obey Hooke's Law. Both equations are explained in more detail below. A spring may provide a compliance (displacement) to a surface or surfaces to which the spring is joined. Where more than one spring provides "a compliance" herein, said compliance is calculated using known physics and mathematical principles governing springs in parallel and series.

"Compliant," in reference to a mechanism or a portion of a mechanism, means that the mechanism or the portion of the mechanism comprises compliance values substantially throughout the entire mechanism or entire portion, respectively, at an operating force. The compliance values may be the same or may vary throughout the given compliant portion.

"Operating force" refers to any force suitable for performing a desired operation.

"Rigid," in reference to a mechanism or a portion of a mechanism, means that the mechanism or portion is substantially without compliance (i.e., with less than 5 microns of compliance), from a spring or otherwise, when an operating force is applied.

"Pressure applying member" refers to any element on a surface of a roll or other equipment that is capable of bonding two or more substrates.

"Substrate" refers to a material which is primarily two-dimensional (i.e. in an XY plane) and whose thickness (in a Z direction) is relatively small (i.e. $\frac{1}{10}$ or less) in comparison to its length (in an X direction) and width (in a Y direction). Non-limiting examples of substrates include a web, layer or layers or fibrous materials, nonwovens, films, and foils such as polymeric films or metallic foils. These materials may be used alone or may comprise two or more layers laminated together.

"Ultimate" refers to material failure due to subjecting a material to mechanical stress past the ultimate stress of the material.

"Yield" refers to permanent and non-reversible material displacement due to subjecting a material to mechanical stress past the yield stress of the material and/or permanent and non-reversible material displacement due to subjecting the material to temperatures higher than the melting point of the material.

"Machine direction" or "MD" refers to the direction of material flow through a process. In addition, relative placement and movement of material may be described as flowing in the machine direction through a process from upstream in the process to downstream in the process.

"Cross direction" or "CD" refers to a direction that is generally perpendicular to the machine direction.

"Z-direction" as used herein, is the direction perpendicular to both the machine and cross directions.

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pant-type diapers, refastenable diapers, incontinence briefs and undergarments, diaper holders and liners, feminine hygiene garments such as sanitary napkins, panty liners, tampons, interlabial devices, absorbent inserts, and the like. Various absorbent articles described above will typically comprise a liquid pervious topsheet, a liquid impervious backsheet joined to the topsheet, and an absorbent core between the topsheet and backsheet. Nonlimiting examples of absorbent articles in various suitable configurations are disclosed in U.S. Pat. Nos. 5,167,897; 5,360,420; 5,599,335; 5,643,588; 5,674,216; 5,702,551; 5,968,025; 6,107,537; 6,118,041; 6,153,209; 6,410,129; 6,426,444; 6,586,652; 6,627,787; 6,617,016; 6,825,393; 6,861,571 and 6,120,487.

"Joined" refers to configurations whereby an element is directly secured to another element by fixedly attaching or removably attaching the element directly to the other element, and configurations whereby an element is indirectly secured to another element by fixedly attaching or removably attaching the element to intermediate member(s) which in turn are fixedly attached or removably attached to the other element.

"Sanitary tissue product" as used herein means a soft, relatively low density fibrous structure useful as a wiping implement for post-urinary and post-bowel movement cleaning (toilet tissue), for otorhinolaryngological discharges (facial tissue), multi-functional absorbent and cleaning uses (paper towels) and wipes, such as wet and dry wipes.

Overview

The present disclosure relates to an apparatus and process for the modification of substrates, including but not limited to bonding, embossing, cutting substrates and combinations thereof. In nonlimiting examples, the modified substrates may be used as, or incorporated into, soluble unit dose fabric and dish care pouches, sanitary tissue products and/or absorbent articles. The modification of a substrate occurs at or near a nip between a tooling agent (e.g., bonding tool, a cutting element) and an anvil (i.e., an additional mechanism that cooperates with the tooling agent to facilitate the intended action). In certain embodiments, the tooling agent is disposed on or in the form of a roll and rotates about an axis. Additionally, or alternatively, the anvil may also be in the form of a roll and rotate about an axis. The anvil may comprise one or more spring elements, which comprise a compliance and provide flexure to the anvil. In some embodiments, the tooling agent also comprises compliance. The compliance of the anvil roll may work in conjunction with the compliance of the tooling roll to provide the desired flexure and/or performance. Additional details are discussed below.

Anvil

Figure 2:
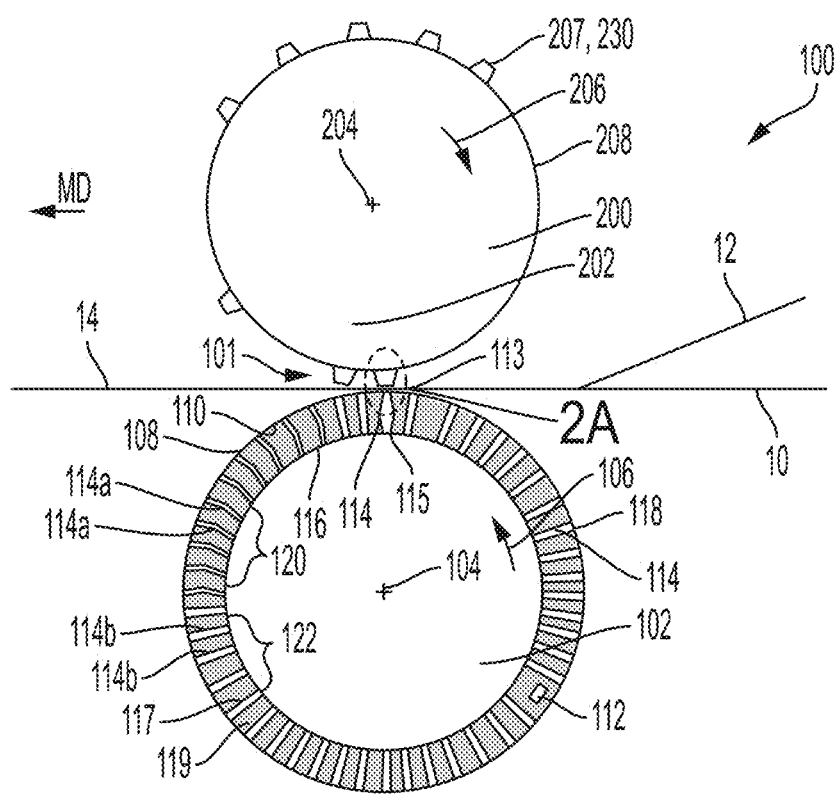
FIG. 2 is a side elevation view of an apparatus.

FIGS. 1 and 2 depict an exemplary apparatus 100, which can be used for converting a substrate 10. Converting functions include bonding, embossing, cutting, printing and the like. The apparatus includes an anvil 102. The anvil 102 may be in the form of a roll as is shown in the figures. The anvil roll 102 may be engageable with a tooling agent 200, which comprises a tool (e.g., knife, nubs, depressions) that initiates or is otherwise necessary for the function. The tooling agent may be selected from the group comprising a bonder (such as a bonding roll), a knife (including cutting elements disposed on rolls), printing tools (such as gravure rolls), and combinations thereof. The exemplary tooling agent in FIGS. 1 and 2 is a bonding roll 202. Although shown in the form of rolls, it is also contemplated that the anvil and/or the tooling agent may not be cylindrical. For example, a servo driven, pitchless tool may be used. Any suitable type and combination of anvils and tooling agents are included to the extent workable under the teachings of this disclosure.

The anvil 102 and tooling agent 200 may be positioned such that a nip 101 is defined between the two mechanisms. As shown in FIG. 2, the anvil roll 102 may comprise an outer circumferential surface 108, and the tooling roll 200 may comprise an exterior circumferential surface 208, which may further include a protrusion 207. The nip 101 may be defined between the outer circumferential surface 108 and the exterior surface 208 or protrusion 207. A substrate 10 may be advanced through the nip in a machine direction (MD), and the anvil and the tooling agent are operatively engageable at the nip such that they provide a desired conversion on the substrate 10 at or near the nip. In the nonlimiting example shown in FIGS. 1 and 2, a first substrate 10 and second substrate 12 are bonded at the nip to form a laminate 14. It is also contemplated that a single substrate may be bonded. For example, a single substrate may be folded and undergo bonding.

During the operation, the anvil roll 102 may rotate in a first rotation direction 106 around the axis of rotation 104 of the anvil roll. The tooling roll may rotate in a second rotation direction 206, opposite the first rotation direction 106 about the axis of rotation 204 of the tooling roll. The rolls 102, 200 may move at the same speeds or different speeds.

It is to be appreciated that the apparatus 100 may also be configured in various ways. For example, each mechanism may independently be a single speed device, a variable speed device, an intermittent speed device, or a cyclically variable speed device. In some embodiments, different types of motor arrangements may be used to rotate the anvil roll 102 and the tooling roll 200. For example, the rolls may be driven independently with two independent motors. Or, a motor may be used to directly drive the tooling roll via pulley and belt drive the anvil roll. Or, when bearer rings are used, only one of the rolls may be driven, and the other roll is driven by the contact surfaces of the bearer rings.

The axis of the anvil may be stationary. In other words, during operation, the anvil as a whole does not shift. Additionally, or alternatively, the axis of the tooling roll may be stationary such that the tooling roll as a whole does not shift during operation. Additional details regarding the interaction of the anvil and tooling agent are discussed in the sections below.

The anvil may comprise an outer surface 108, such as the outer circumferential surface 108 shown in FIG. 2. The anvil may further comprise an opposing surface 110, opposite the outer surface, and an inner surface 116. The inner surface 116 may be an inner circumferential surface 116 as shown in FIG. 2 and may be disposed radially inward of the outer circumferential surface and in facing relationship with the opposing surface 110. Each of the surfaces may be continuous. Alternatively, one or more of the surfaces may be discontinuous. The outer surface may be a substantially smooth anvil surface or may have a patterned anvil surface. For example, the patterned anvil surface can include an array of anvil elements or members that cooperatively match a pattern of tooling elements such as pressure applying members or cutting elements.

Figure 2A:
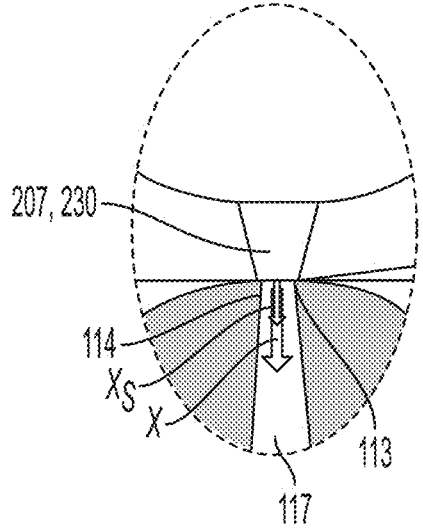
FIG. 2A is an enlarged view of the encircled portion of FIG. 2.
Figure 3:
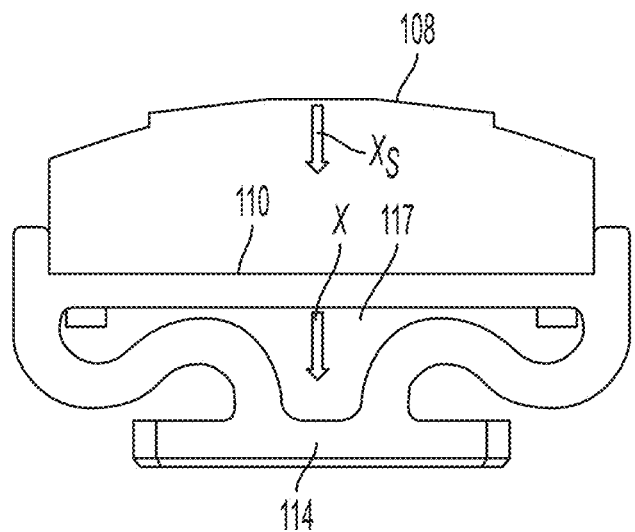
FIG. 3 is a side elevation view of a spring element joined to a portion of an anvil.

The anvil may further comprise one or more spring elements 114. When an operating force is applied, the spring elements may each comprise a compliance, x, as shown in FIG. 2A, for example, and discussed in more detail below. Generally, compliance is the displacement vector the spring element experiences when force is applied. The spring elements may compress when the anvil engages with the tooling agent at the nip. Further, the displacement of the spring may result in displacement of the surface of the anvil, $x_s$, as illustrated in FIGS. 2A and 3 for example and discussed further below.

Figure 5:
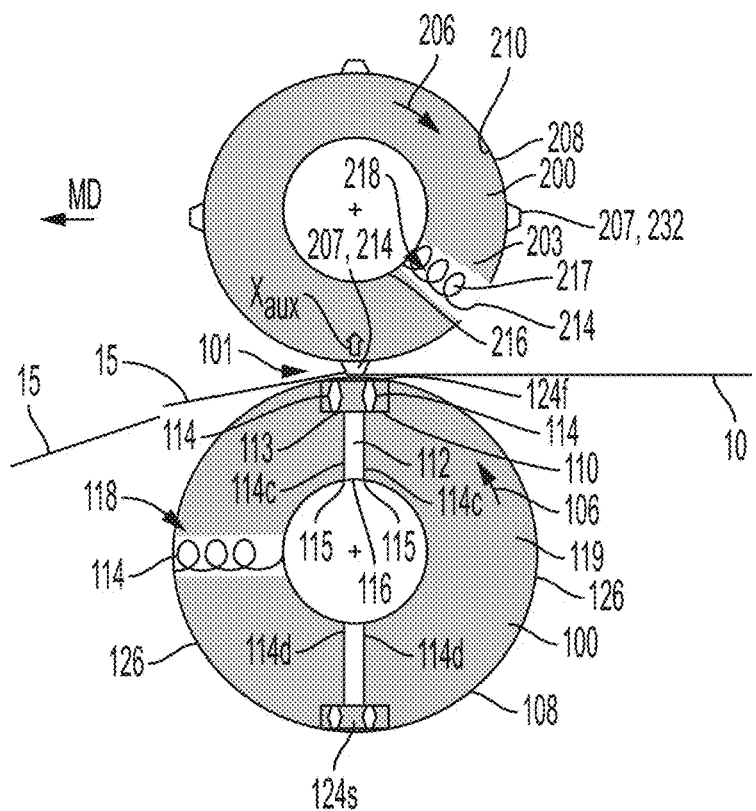
FIG. 5 is a side elevation view of an apparatus.

Returning to FIG. 2, the spring elements may be positioned between the opposing surface 110 and the inner surface 116. A spring element may be joined to the opposing surface and/or the inner surface or integrally formed with either or both surfaces. A spring element 114 may comprise a proximal end portion 113 and a distal end portion 115. The proximal end portion 113 may be joined to the opposing surface 110 and the distal end portion 115 may be joined to the inner surface 116. Additionally, or alternatively, one or more spring elements 114 may be disposed between the outer surface 108 and the opposing surface 110 as shown in FIG. 5, which depicts anvil in operative relationship with a roll comprising a knife (referred to as a knife roll 203 herein) which cuts a substrate 10 into pieces 15. Any suitable configuration of spring elements within the roll is contemplated.

The spring elements 114 may be in a variety of shapes, including linear and/or curvilinear, and sizes as shown in FIGS. 2 through 5. Spring elements can be formed from materials having differing material properties in order to provide differential properties to the anvil (e.g., flexural modulus, spring constants, compliance). A spring element may comprise different constituent material than another spring element and/or different constituent material from the anvil at areas where spring elements do not exist. The shape, size and/or material of a spring element may be specific to the amount of compressibility in the anvil and/or desired in the anvil. Additionally, or alternatively, the shape, size and/or material of the spring element may be specific to the amount of force the anvil may withstand while being operatively engaged by the tooling agent. Likewise, spring elements in the anvil can be designed with consideration to force and compressibility constraints of tooling agents.

The spring elements 114 may be positioned in a reduced stiffness area 118. In the reduced stiffness area, the constituent material(s) of the anvil are thinner, removed or otherwise adapted to reduce the stiffness of said area as compared to an unadapted area 119 (which is represented by gray shading in FIGS. 2 and 5). In some embodiments, the anvil comprises a composite material, and the reduced stiffness area is formed from one material while the unadapted area is formed from another material. An anvil comprising a composite material may be formed by additive manufacturing.

Figure 4:
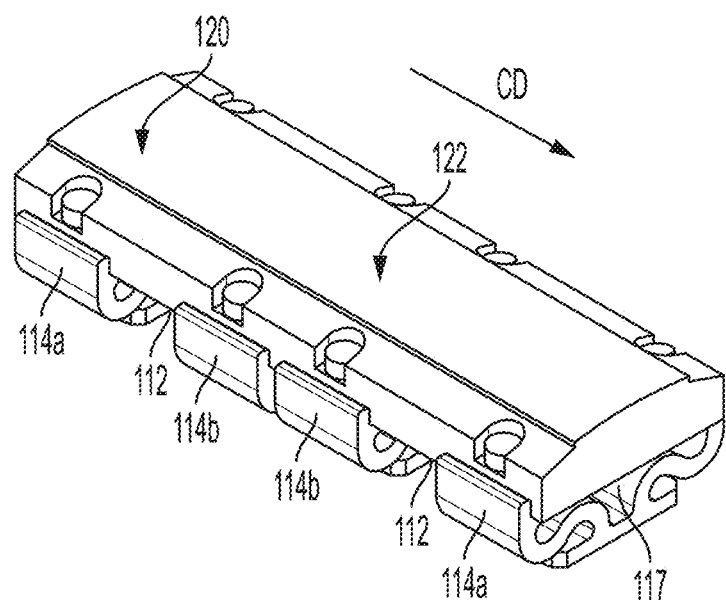
FIG. 4 is a perspective view of spring elements joined a portion of an anvil.

As shown in FIGS. 2-4, the spring themselves may comprise open areas 117 (void of material or having reduced amounts of material), which contribute to reduced stiffness. Additionally, or alternatively, adjacent spring elements 114 may be separated by voids 112 (i.e., lack of material), reduced material areas (as compared to unadapted areas) or combinations thereof as shown in FIGS. 2 and 5. The reduced stiffness areas provide flexure to the anvil without exceeding the strength of the constituent material of the anvil. The reduced stiffness areas may be designed to provide the desired flexure without exceeding the yield strength of the constituent anvil material, and therefore the anvil may exhibit greater fatigue resistance as compared to a conventional anvil. The reduced stiffness areas may also be designed such that the ultimate strength of the constituent material of the anvil is not exceeded.

In some embodiments, reduced stiffness areas and/or spring elements are disposed substantially throughout the entire anvil such that the anvil is continuously compliant as illustrated in FIG. 2. In some embodiments, the spring elements and/or reduced stiffness areas may be disposed such that at least 75%, or at least about 85%, or at least about 90%, or at least about 95%, or from about 75% to about 100%, of a portion of the anvil engaged with the tooling agent is compliant, reciting for said range every 1% increment therein. Compliance values throughout the anvil may be the same or may differ.

It is to be appreciated that each spring element may be a linear spring (i.e., obeys Hooke's law) or a non-linear spring, (i.e., does not obey Hooke's law). One of skill in the art will appreciate that a linear spring is understood to mean that as long as each spring element 114 is not stretched or compressed beyond its elastic limit, the spring element 114 of will obey Hooke's law, which states that the force with which the spring element 114 pushes back is linearly proportional to the distance from its equilibrium length such that:

$$\sigma = E\epsilon$$

where:
 σ=Stress;
 E=Modulus of Elasticity; and,
 ϵ=Axial Unitary Deformation.
The above equation may be re-written as:

$$F = -kx$$

where:
 F=resulting force vector (i.e., the magnitude and direction of the restoring force the spring exerts);
 k=spring constant (e.g., also the force constant, or stiffness, of the spring). This is a constant that depends on the spring's material, shape, and/or construction. The negative sign
 indicates the force exerted by the spring is in the direction opposite its displacement; and,
 x=displacement vector (i.e., the distance and direction the spring is deformed from its equilibrium length; also referred to herein as compliance).

According to this formula, a graph of the force F as a function of the displacement x will be a straight line passing through the origin, whose slope is k. In other words, the spring constant is a characteristic of a spring which is defined as the ratio of the force affecting the spring to the displacement caused by it. By way of example, springs suitable for use as a spring element 114 may include coil springs and other common springs that obey Hooke's law. Springs suitable for use as a spring element 114 may be based on simple beam bending that may produce forces that vary non-linearly with displacement. Further, if made with constant pitch (wire thickness), conical springs may have a variable rate. However, a conical spring suitable for use as a spring element 114 may be made to have a constant rate by creating the spring with a variable pitch. A larger pitch in the larger-diameter coils and a smaller pitch in the smaller-diameter coils will force the spring to collapse or extend all the coils at the same rate when deformed.

Since force is equal to mass, m, times acceleration, a, the force equation for a spring obeying Hooke's law provides:

$$F = ma \rightarrow -kx = ma$$

It may be preferred that the mass of the spring element 114 be small in comparison to the mass of interacting component of the tooling agent (e.g., a bonding surface, a cutting element), such that the mass of the spring element can be ignored. Since acceleration is simply the second derivative of x with respect to time, $$-kx = m\frac{d^2x}{dt^2}$$

This is a second order linear differential equation for the displacement as a function of time. Re-arranging:

$$\frac{d^2x}{dt^2} + \frac{k}{m}x = 0$$

the solution of which is the sum of a sine and cosine:

$$x(t) = A\sin\left(t\sqrt{\frac{k}{m}}\right) + B\cos\left(t\sqrt{\frac{k}{m}}\right)$$

where:
 A, B=arbitrary constants that may be found by considering the initial displacement and velocity of the mass.

As would be understood by one of skill in the art, a spring can be seen as a device that stores potential energy, specifically elastic potential energy, by straining the bonds between the atoms of an elastic material. Hooke's law of elasticity states that the extension of an elastic rod (e.g., its distended length minus its relaxed length) is linearly proportional to its tension, the force used to stretch it. Similarly, the contraction (i.e., negative extension) is proportional to the compression (i.e., negative tension).

Hooke's law is a mathematical consequence of the fact that the potential energy of the rod is a minimum when it has its relaxed length. Any smooth function of one variable approximates a quadratic function when examined near enough to its minimum point as can be seen by examining the Taylor series. Therefore, the force—which is the derivative of energy with respect to displacement—will approximate a linear function. The force of a fully compressed spring is provided as:

$$F_{max} = \frac{Ed^4(L - nd)}{16(1 + v)(D - d)^3 n}$$

where:
 E=Young's modulus;
 d=spring wire diameter;
 L=free length of spring;
 n=number of active windings;
 v=Poisson ratio; and,
 D=spring outer diameter.

One of skill in the art will appreciate that a non-linear spring utilized for a spring element 114 is understood to mean that a non-linear relationship exists between the force applied to the spring and the spring's resulting displacement. The skilled artisan will appreciate that a graph showing force vs. displacement for a non-linear spring will be more complicated than a straight line, with a changing slope. Stated differently, a non-linear spring element does not obey Hooke's law, and as such, the applied force is related to the relative displacement according to the formula:

$$F = k*f(x)$$

where:
 F=applied force;
 x=spring displacement vector from the spring's neutral position (i.e., compliance); and,
 k=spring constant (i.e., stiffness).
The resulting spring constant is provided as:

$$k = \frac{dF}{dx}$$

Therefore, it should be understood that a spring element 114 suitable for use in the anvil may include all springs, no matter the design or shape that obey, or do not obey, Hooke's law. Further, spring elements 114 comprising any combination of linear and non-linear springs may be suitable for use in the anvil. In other words, any suitable combination of spring elements may include all springs, no matter the design, matter of construction, or shape that obey, or do not obey, Hooke's law that are suitable for use in the anvil in order to provide the desired degree of localized deformation.

Each spring element may comprise a compliance of at least about 5 microns, or at least about 10 microns, or at least about 12 microns, or at least about 15 microns, or at least about 20 microns, or at least about 50 microns, or at least about 70 microns, up to 250 microns, or about 5 to about 250 microns, or from about 10 to about 150 microns, or from about 10 microns to about 70 microns, in a direction, reciting for each interval every 1 micron increment therein. Any workable compliance value is contemplated. In some embodiments, the direction is radially inward. Spring elements may be displaced in different directions, which may provide additional flexibility in operation and process design.

It is also contemplated that the position and/or sizes of spring elements in a plurality may be such that an individual spring element's compliance is insignificant by itself, but rather the combination of a plurality of spring elements results in the recognizable displacement of a portion of the anvil during operation. In such examples, the compliance is the combination of compliance values from the spring elements in the plurality, as calculated using known physics and mathematical principles for combining properties of springs. For example, a force may be applied to a region where multiple springs are disposed. Compliance in said region may be determined by the effect of all of the springs rather than an individual spring. Similarly, two springs may act upon the same location, and compliance at said location may be determined by the contribution of both springs.

Spring elements 114 within the anvil may be provided with the same spring constant or different spring constants. In other words, as shown in FIG. 2, a first spring element 114a may be provided with a first spring constant, $k_1$, and a second spring element 114b may be provided with a second spring constant, $k_2$. The first spring constant, $k_1$, may be different from the second spring constant, $k_2$ (e.g., the first spring constant, $k_1$, may be less than the second spring constant, $k_2$, or the first spring constant, $k_1$, may be greater than the second spring constant, $k_2$). Likewise, spring elements 114 may be provided with the same compliance or different compliance values. For instance, the anvil may comprise one or more first spring elements 114a and one or more second spring elements 114b. The first spring elements may be provided with a first compliance, and second spring elements 114b may be provided with a second compliance, $x_2$, different from the first compliance. The first and second compliance may differ in magnitude by at least about 5%, or at least about 10%, or from about 5% to about 1000%, or from about 10% to about 800%, or from about 15% to about 750%, or from about 20% to about 600%, reciting for each range every 10% increment therein. In some embodiments, one anvil roll can be used in conjunction with two or more tooling agents or operations. In such embodiments, larger differences in compliance may be desirable. Likewise, the first and second compliance may differ in direction.

The first spring elements 114a may be disposed such that at least 75%, or at least about 85%, or at least about 90%, or at least about 95%, or from about 75% to about 100% of a first region 120 is compliant. The second spring elements 114b may be disposed such that at least 75%, or at least about 85%, or at least about 90%, or at least about 95%, or from about 75% to about 100% of a second region 122 is compliant. The first region may comprise the first compliance, $x_1$, and the second region may comprise the second compliance, $x_2$. The compliance of the first region may differ from the compliance of the second region in magnitude by at least about 5%, or at least about 10%, or from about 5% to about 1000%, or from about 10% to about 800%, or from about 15% to about 750%, or from about 20% to about 600%, reciting for each range every 10% increment therein. The regions may differ in the direction of compliance. It is also contemplated that the first region and/or second region may independently comprise spring elements having different compliance values within the respective region. Spring elements in a plurality may include different properties such that the compliant region reacts in a certain way when engaged with the tooling agent.

In some embodiments, the first region 120 may be disposed at a first MD position, and the second region 122 may be disposed at a second MD position, as shown in FIG. 2, for example. The first and second MD positions may be adjacent or may be separated by a distance in the MD of at least 5%, or at least about 10%, or at least about 15%, or at least about 25% of the MD length (or circumference) of the outer surface 108. Additionally, or alternatively, the first region 120 may be disposed at a first CD position, and the second region 122 may be disposed at a second CD position, as shown in FIG. 1. The first and second CD positions may be adjacent or may be separated by a distance in the CD of at least 5%, or at least about 10%, or at least about 15%, or at least about 25% of the CD width of the outer surface 108.

In nonlimiting examples, a region may comprise an area of at least 5%, or at least 10%, or at least 15%, or at least 25% of the surface area of the outer surface. In further nonlimiting examples, a region may comprise an area of at least 5%, or at least 10%, or at least 15%, or at least 25% of the surface area of the opposing surface. Different regions may comprise the same area or different areas.

Varying the spring constants and/or compliance values provides the anvil with the ability to have a localized, discrete, flexural modulus thereby increasing the operable lifetime and reducing potential catastrophic degradation. In mechanics, the flexural modulus or bending modulus, E, is an intensive property that is computed as the ratio of stress to strain in flexural deformation, or the tendency for a material to bend. It is determined from the slope of a stress-strain curve produced by a flexural test (such as ASTM D790) and has units of force per area.

For a 3-point test of a rectangular beam behaving as an isotropic linear material, where w and h are the width and height of the beam, I is the second moment of area of the beam's cross-section, L is the distance between the two outer supports, and d is the deflection due to the load F applied at the middle of the beam, the flexural modulus, E, is provided by:

$$E_{bend} = \frac{L^3 F}{4 w h^3 d}$$

From elastic beam theory, the deflection, d, is provided as:

$$d = \frac{L^3 F}{48 I E}$$

For a rectangular beam, the moment, I, is provided by:

$$I = \frac{1}{12}wh^3$$

Thus:

$E_{bend}=E$ (i.e., Elastic modulus)

One of skill in the art will recognize that ideally flexural or bending modulus of elasticity is equivalent to the tensile or compressive modulus of elasticity. These values may be different, especially for plastic materials. However, the skilled person will recognize that each spring element or sets of spring elements 114 can provide discrete and distinct flexural modulus for portions of the anvil.

During operation, compliance may occur at the nip. Stated differently, force will be applied at the nip and the spring element(s) will undergo displacement. Returning to FIG. 2A, spring elements may be disposed such that surface compliance is achieved. That is, spring elements may be disposed such the outer surface 108 or a surface below the outer surface of the anvil is displaced (i.e., has a surface compliance, $x_s$). The surface compliance may exist at the location where the spring element is in contact with the anvil and/or in areas adjacent to said location. Additionally, or alternatively, spring elements may be disposed to displace a surface below the outer surface (i.e., a surface below the outer surface may have a compliance). The surface compliance, $x_s$, may be equal to, or within 10% of, the spring compliance, x, at said location.

It is also to be appreciated that the spring elements 114 may be arranged as pairs of spring elements as shown in FIG. 5 for example, where a pair of primary springs 114c are separated by a void 112. Each spring element of a pair of spring elements may be joined at a proximal end 113 to the opposing surface 110 and a distal end 115 of each spring element may be joined to the inner surface 116. In this arrangement, a first spring element of a pair of spring elements may deflect in a first direction in a first combination of the MD, CD, and/or Z-directions relative to the inner surface 116 and a second spring element of a pair of spring elements may deflect in a second direction in a second combination of the MD, CD, and/or Z-directions relative to the inner surface. This may acceptably accommodate any torsional forces applied to and experienced by the anvil when the anvil is operatively engaged with an opposed tooling agent. Likewise, a spring element may be designed to have two opposing arm elements which may operate in the same manner as pairs of springs. For instance, the exemplary spring in FIG. 3 will deflect forces in a similar manner to using a pair of discrete spring elements.

Stated another way, it is to be appreciated that providing the plurality of spring elements as arranged pairs of spring elements (or configured to generate the same benefits as a pair of spring elements) may facilitate the deflection of the anvil into any desired combination of the MID, CD, and/or Z-directions. The skilled person will appreciate that the forces disposed upon the anvil roll by an opposed tooling roll and any substrate disposed therebetween may not be solely limited to forces in the Z-direction. Therefore, providing sections of the anvil with the possibility for three-dimensional movement due to the individual flexion provided by each spring element of a given pair of spring elements may reduce any wear caused by repeated out-of-plane deformation of the anvil that may result in rapid degradation of the outer surface 108.

Figure 6:
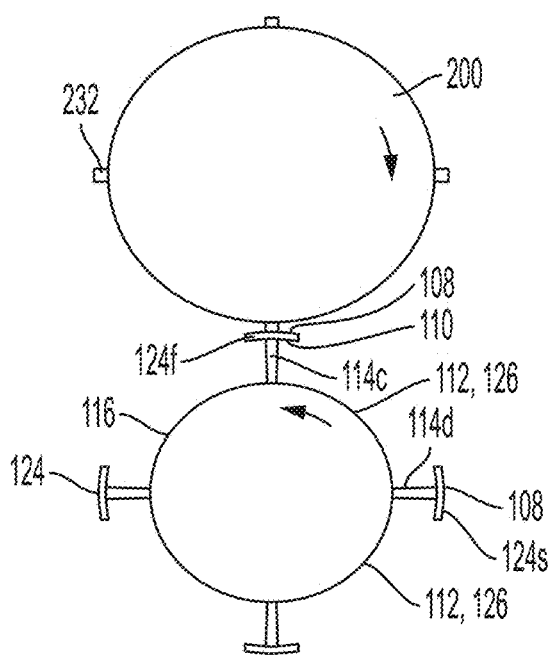
FIG. 6 is a side elevation view of an apparatus.

In certain embodiments shown in FIGS. 5-6, the anvil may comprise one or more engaging portions 124 and one or more passive portions 126. In operation, an engaging portion 124 interacts with the tooling agent while a passive portion 126 does not. In nonlimiting examples, the passive portion 126 may be substantially rigid under operating forces. The passive portions may be unadapted portions 119. The engaging portion may be operatively engageable with a tooling agent by the design of the tooling agent (e.g., the tooling agent has protrusions which interact with the engaging portion), the design of the anvil (e.g., engaging portions are disposed radially outward of the passive portions), changes in material on the anvil and/or tooling agent, variations in the substrate, combinations of the foregoing or any known means of effecting interaction between the two mechanisms. Additionally, or alternatively, as shown in FIG. 6, the anvil may comprise voids 112 between engaging portions 124 such that the outer surface 108 is discontinuous.

The anvil may comprise one or more primary spring elements 114c which provide a primary compliance to a first engaging portion 124f. The primary compliance may be at least about 5 microns, or at least about 10 microns, or at least about 12 microns, or at least about 15 microns, or at least about 20 microns, or at least about 50 microns, or at least about 70 microns, up to 250 microns, or about 5 to about 250 microns, or from about 10 to about 150 microns, or from about 10 microns to about 70 microns, in a first direction, reciting for each interval every 1 micron increment therein. In some embodiments, the first direction is radially inward. The primary spring elements may have any of the features described above with respect to spring elements.

The anvil may further comprise a second engaging portion 124s and one or more secondary spring elements 114d, which provide a secondary compliance to the second engaging portion 124s. The secondary compliance may be at least about 5 microns, or at least about 10 microns, or at least about 12 microns, or at least about 15 microns, or at least about 20 microns, or at least about 50 microns, or at least about 70 microns, up to 250 microns, or about 5 to about 250 microns, or from about 10 to about 150 microns, or from about 10 microns to about 70 microns, in a second direction, reciting for each interval every 1 micron increment therein. The secondary compliance may be the same as the primary compliance. Alternatively, the secondary compliance may differ from the primary compliance. In nonlimiting examples, the secondary compliance may differ from the primary compliance in magnitude by at least about 5%, or at least about 10%, or from about 5% to about 1000%, or from about 10% to about 800%, or from about 15% to about 750%, or from about 20% to about 600%, reciting for each range every 10% increment therein. In some embodiments, the second direction is radially inward. The second direction may be the same as the first direction or may be different from the first direction. The secondary spring elements may comprise any of the features described above with respect to spring elements.

The anvil may be manufactured in the form of a unibody construction, through use of techniques such as SLA/stereo lithography, SLM/Selective Laser Melting, RFP/Rapid freeze prototyping, SLS/Selective Laser sintering, EFAB/Electrochemical fabrication, DMDS/Direct Metal Laser Sintering, LENS/Laser Engineered Net Shaping, DPS/Direct Photo Shaping, DLP/Digital light processing, EBM/Electron beam machining, FDM/Fused deposition manufacturing, MJM/Multiphase jet modeling, LOM/Laminated Object manufacturing, DMD/Direct metal deposition, SGC/Solid ground curing, JFP/Jetted photo polymer, EBF/Electron Beam Fabrication, LMJP/liquid metal jet printing, MSDM/Mold shape deposition manufacturing, SALD/Selective area laser deposition, SDM/Shape deposition manufacturing, combinations thereof, and the like. However, the skilled person will recognize a unibody anvil may be constructed using these technologies in combination with other known techniques such as casting.

Further, the anvil may be manufactured from conventional machining techniques utilizing manually controlled devices, such as hand wheels or levers, or mechanically automated devices. The anvil may be manufactured using Computer Numeric Control (CNC) automated machine tools, which may provide end-to-end component design using computer-aided design (CAD) and computer-aided manufacturing (CAM) programs. CNC may include laxer cutting, welding, friction stir welding, ultrasonic welding, flame and plasma cutting, bending, spinning, hole-punching, pinning, gluing, fabric cutting, sewing, tape and fiber placement, routing, picking and placing and sawing.

Alternatively, the anvil may be manufactured from multiple materials in order to utilize unique physical characteristics of the material forming each part. By way of nonlimiting example, the outer surface 108 may be formed from a first material having a first set of material properties and the spring elements 114 may be formed from a second material having a second set of material properties. Likewise, various spring elements may be formed from materials with differing material properties in order to provide a differential flexural modulus to a respective portion of the anvil.

In some embodiments, portions of the anvil may be fabricated separately and combined. This may facilitate assembly and repair work to parts of the anvil such as coating, machining, heating and the like. In such techniques, two or more of the components of the anvil commensurate in scope with the instant disclosure may be combined into a single integrated part.

Tooling Agent

The tooling agent 200 may be any tool that operates with an anvil at a high-pressure nip. In some embodiments, the apparatus 100 is configured to include a nip pressure above 20,000 PSI between the tooling agent and the anvil. In some embodiments, the apparatus 100 is configured to define a nip pressure from about 20,000 PSI to about 200,000 PSI, or from about 60,000 PSI to about 150,000 PSI. The pressure at the nip may depend, in part, on the contact area, the basis weight of the substrate, the modulus of the substrate, the type of substrate, and the speed at which the operation is completed, for example. The nip pressure may be any suitable pressure at which the desired operation can be performed.

The tooling agent 200 may be selected from the group consisting of bonding tools 202, cutting tools 203 (including tools comprising a curvilinear knife), and combinations thereof. In nonlimiting examples, the tooling agent 200 is in the form of a roll as shown in the figures. The roll may comprise an exterior circumferential surface 208, an opposing tooling roll surface 210, and an interior circumferential surface 216 as shown in FIG. 5. Alternatively, the tooling agent may be non-cylindrical.

In some embodiments, the tooling agent 200 may be substantially rigid under operating forces. In other embodiments, one or more portions of the tooling agent may comprise an auxiliary compliance $x_{aux}$. The auxiliary compliance may be in a direction that is different from the direction of compliance in the anvil roll. For instance, at the nip, the auxiliary compliance may be in the opposite direction of the anvil compliance. The auxiliary compliance may be in a radially inward direction (radially inward with respect to the tooling roll) as shown in FIG. 5. The magnitude of the auxiliary compliance may be the same as or differ from the magnitude of the compliance in the anvil.

The auxiliary compliance may comprise a surface compliance such that a surface of the tooling agent is displaced. The auxiliary compliance may be provided by one or more spring elements 214 in or on the tooling agent. The tooling spring elements 214 may be disposed between the interior surface 216 and the opposing tooling surface 210. Additionally, or alternatively, tooling spring elements 214 may be disposed outward of the exterior surface, such as in a protrusion. The protrusion may be integrally formed with the exterior surface or joined to the surface. In some nonlimiting examples, protrusions 207 may comprise pressure applying members 230, as shown for example in FIG. 2. Pressure applying members may extend radially away from the outer circumferential surface 208 of a bonding roll and may be any suitable shape, size or pattern. At the nip, the pressure applying members compress one or more substrates between the pressure applying member and the anvil. In turn, the pressure generated at the nip causes the substrate(s) to yield and form a bond. The ultimate strength of the substrate(s) should not be exceeded during operation as doing so could cause tears and holes. By embodying tooling spring elements in pressure applying members, the pressure applying members may be compressible, reducing the likelihood of reaching the materials' ultimate strength and thereby allowing greater variance in operating parameters while still producing effective bonds and longer equipment life.

In other nonlimiting examples, protrusions may comprise cutting elements 232, as shown for example in FIG. 5. Cutting elements may comprise linear or curvilinear cutting edges or blades. In addition, cutting elements may comprise continuous or intermittent cutting edges or blades. Intermittent cutting edges may be formed from a single material or a plurality of discrete segments. As stated above, cutting operations may require interference between the cutting element and anvil. By disposing spring elements within the cutting tool, greater variance in operating parameters (such as the amount of interference) and longer equipment life is provided.

Exemplary tooling spring configurations are disclosed in commonly assigned U.S. patent application Ser. No. 15/446,378 and 62/595,606. Spring elements in the tooling agent may comprise any of the features taught above with respect to spring elements in the anvil. Likewise, spring elements in the tooling agent may be disposed in reduced stiffness areas 218 and/or comprise open areas 217. In some nonlimiting examples, auxiliary compliance may be provided by reduced stiffness areas alone. For example, a knife may comprise one or more reduced stiffness areas which provide flexure to the knife and transfers stress to the tooling roll as opposed to concentrating the stress on the knife itself, as is disclosed in U.S. patent application Ser. No. 15/446,378.

The auxiliary compliance may be at least about 5 microns, or at least about 10 microns, or at least about 12 microns, or at least about 15 microns, or at least about 20 microns, or at least about 50 microns, or at least about 70 microns, up to 250 microns, or about 5 to about 250 microns, or from about 10 to about 150 microns, or from about 10 microns to about 70 microns, in a direction, reciting for each interval every 1 micron increment therein. In some embodiments, the direction is radially inward. As with the anvil, the tooling agent may be designed such that the anvil is continuously compliant. The tooling agent may be designed such that at least 75%, or at least about 85%, or at least about 90%, or at least about 95%, or from about 75% to about 100%, of a portion of the tooling agent that is engageable with the anvil is compliant, reciting for said range every 1% increment therein. Likewise, as taught above with respect to the anvil, the tooling agent may comprise compliant regions, where two regions may differ in the magnitude and/or direction of compliance.

Design of the Apparatus

The apparatus may be designed to maximize compliance at operating forces. In some embodiments, compliance provided to the anvil alone or in conjunction with auxiliary compliance in the tooling agent compliance may be at least about 10 microns, or at least about 20 microns, or least about 25 microns, or at least about 30 microns, or about 1500 microns or less, or about 1000 microns or less, or about 750 microns or less, or about 500 microns or less, or from about 5 microns to about 1500 microns, or from about 10 microns to about 1000 microns, or from about 15 microns to about 750 microns reciting for each range every 25 micron increment therein.

The nip pressure may be above 20,000 PSI between the tooling agent and the anvil. In some embodiments, the apparatus 100 is configured to define a nip pressure from about 20,000 PSI to about 200,000 PSI, or from about 60,000 PSI to about 150,000 PSI. The pressure at the nip may depend, in part, on the area of the bond pattern, the basis weight of the substrate, the modulus of the substrate, the type of substrate, the speed of the operation, and the desired interference, for example.

In certain operations, such as bonding, the operative engagement should be such that the ultimate strength of the substrate(s) is not exceeded during operation. If the ultimate substrate strength is exceeded, the substrate may tear or a hole may be created. Engagement between stiffer components (e.g., a rigid anvil and rigid bonding roll) will exceed or at least reach the yield strength and ultimate strength of the material faster than using one or more compliant components. Thus, the addition of a compliant component allows for a greater tolerance in operating parameters because there is a larger range of parameters in which the component may be compressed before the substrate is damaged.

Additionally, with respect to cutting operations, current manufacturing processes can require a large degree of setup in order to provide the exact deformation required for the web material to be cut. It is believed that current manufacturing techniques may require a deformation of the knife and/or the anvil on the order of 1.0 µm to 9.0 µm in order to effectively cut a web material for use as an assembled product such as a diaper, catamenial device, or adult incontinence article. The introduction of compliance to the anvil, and optionally the tooling agent, allows for an operator to place the knife/anvil system in a position without an exacting degree of accuracy while still providing the desired degree of deformation of the knife and/or anvil. As such, setup time is decreased.

Likewise, incorporating compliance into an operation reduces the adverse impact on equipment. Indeed, the yield strength of equipment is reached more quickly when engagement is between stiffer components. As such, the inclusion of compliance may lead to prolonged operating life on both the compliant mechanism (e.g., anvil) and the mechanism with which it engages (e.g., rigid tool). The use of compliant components may also permit the equipment to be made from a more diverse range of materials.

Method

In summary, a method of modifying a web may comprise the steps of rotating an anvil roll about an axis of rotation and rotating a tooling roll adjacent to the anvil such that a nip is formed between the anvil roll and the tooling roll. The anvil roll may comprise one or more spring elements. One or more substrates are advanced through the nip in the machine direction such that the spring elements compress as the anvil roll engages with the tooling roll at the nip. The compression provides compliance to the spring element and/or a surface of the anvil. The anvil roll, tooling roll and their components may have features described above.

Articles

Figure 7:
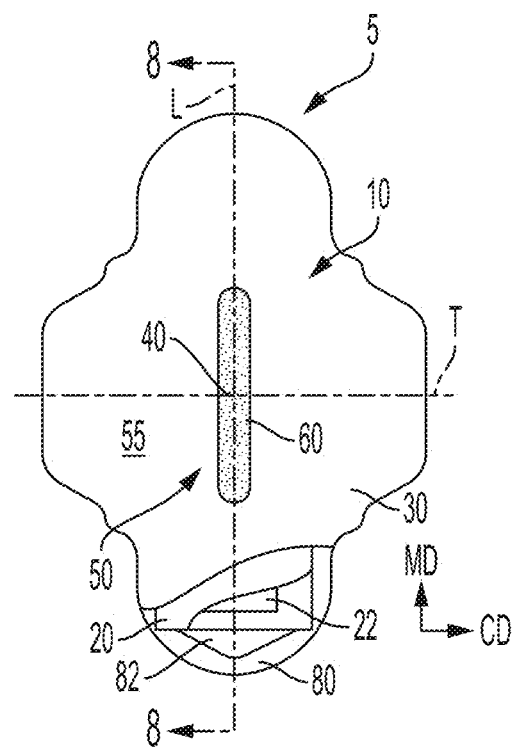
FIG. 7 is a top plan view of an absorbent article.
Figures 8, 9:
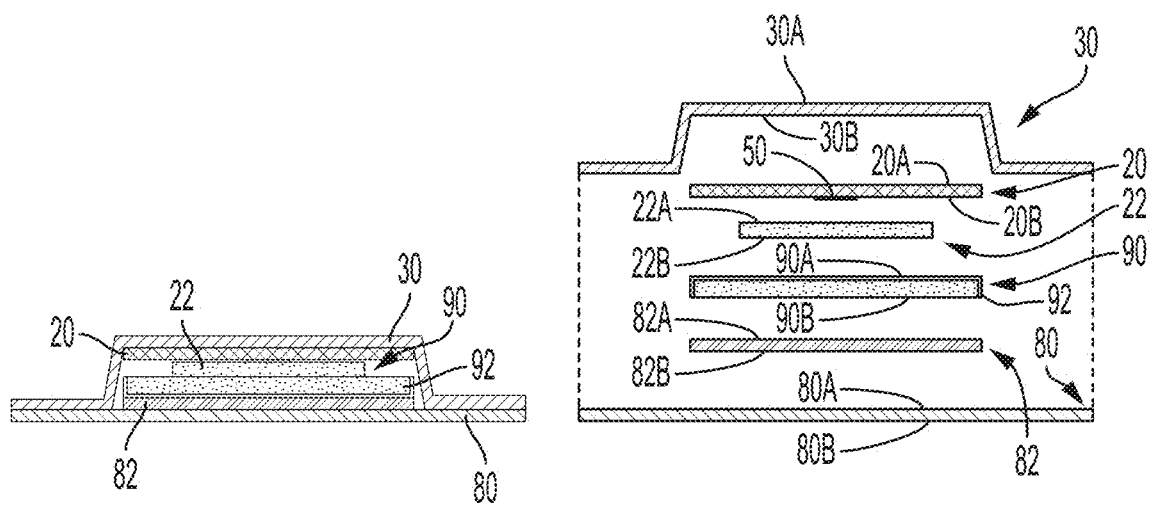
FIG. 8 is a cross-sectional view of the absorbent article taken about line 8-8 of FIG. 7.
FIG. 9 is an exploded view of the absorbent article cross-section of FIG. 8.

The substrate 10 undergoing a modification with the above-described apparatus 100 and/or method can be incorporated into an absorbent article. An exemplary absorbent article 5 according to the present disclosure, shown in the form of a sanitary napkin or incontinence pad, is represented in FIGS. 7-9. This type of absorbent article is shown for illustration purpose only as the present disclosure can be used for making a wide variety of other absorbent articles. FIG. 7 is a top view of the example absorbent article 5, in a flat-out state, with portions of the structure being cut-away to more clearly show the construction of the absorbent article 5. FIG. 8 is a cross-sectional view of the absorbent article of FIG. 7 taken along line 8-8, while FIG. 9 is an exploded cross-sectional view of the absorbent article of FIG. 8. In FIG. 9, numbers followed by A and B indicate the surfaces of the respective layers.

Referring to FIG. 7, the absorbent article 5 can have a substantially planar configuration and a centroid 40. The centroid 40 is the in-plane center of mass of the absorbent article 5. The centroid 40 is at the intersection between the longitudinal centerline L and transverse centerline T. The transverse centerline T is orthogonal to the longitudinal centerline L. The absorbent article 5 can, but need not be, symmetric about the transverse centerline T. The absorbent article 5 has a body-facing surface and a garment facing surface.

The absorbent article 5 comprises a plurality of layers to promote certain liquid handling behaviors. Example layers include a liquid-permeable topsheet 30 and an absorbent core 90. Some embodiments can also include a top core 22. The absorbent core 90 can have a number of suitable arrangements, for example the absorbent core 90 can have a tissue outer wrapping 92 (FIG. 9). The absorbent articles can also have a backing material 82 and a backsheet 80.

To help ensure that fluids flow into the absorbent core 90, some absorbent articles are constructed with what is sometimes referred to as a secondary topsheet 20 ("STS") positioned intermediate the topsheet 30 and the absorbent core 90. This secondary topsheet 20 is designed to acquire the fluid on the liquid-permeable topsheet 30 and distribute it to the underlying absorbent core 90. To help ensure that the secondary topsheet 20 transfers the fluid to the absorbent core 90, the secondary topsheet 20 can have sufficient capillarity to draw the fluid through the liquid-permeable topsheet 30. To ensure that the fluid flow continues onto the absorbent core 90, the secondary topsheet 20 can be designed with more permeability than the absorbent core 90, and less capillarity than the absorbent core 90. For example, a secondary topsheet can be an airlaid-tissue web made from hydrophilic cellulosic fibers and polyethylene powder, sometimes referred to as an airlaid STS. Or, a secondary topsheet can be a spunlace web. A spunlace web may be a hydroentangled fibrous structure with a basis weight between about 35 grams per square meter (gsm) and about 85 gsm. The spunlace web may comprise about 30% to about 60%, by weight, of cellulosic fibers, about 5% to about 30%, by weight, of non-cellulosic fibers, and about 30% to about 55%, by weight, of polyolefin-based binder fibers. Referring back to FIGS. 7 and 8, in one embodiment, the first substrate 20 comprises a secondary topsheet and the second substrate 30 comprises a topsheet. For example, the first substrate 20 may comprise a spunlace STS and the second substrate 30 may comprise a film-nonwoven composite topsheet, such as a polyethylene film-polyethylene nonwoven composite topsheet.

It is to be appreciated that the apparatuses and methods herein can be used to bond various types of substrates together. The substrates may comprise materials that can be deformed beyond their yield point by the compression in the nip of the apparatus. For example, in some embodiments the apparatus may be used to bond nonwoven substrates, such as for example, polypropylene nonwoven, polyethylene film, bi-component nonwoven or film, polyethylene terephthalate nonwoven or film. In some embodiments, the apparatuses and methods herein may be used to bond a substrate which includes a mixture of cellulosic fibers and polyethylene or polyethylene-polypropylene bicomponent fibers or particulate. In some embodiments, the substrates may have a basis weight of about 6 gsm to about 100 gsm. Other types of substrates can be sandwiched in between two layers of nonwovens or films.

The substrates may comprise any suitable woven, nonwoven, film, combination or laminate of any of the foregoing materials. Non-limiting examples of suitable substrates include cellulose, films, such as polymeric or thermoplastic films, foils, such as metallic foils (e.g. aluminum, brass, copper, and the like), webs comprising sustainable polymers, foams, fibrous nonwoven webs comprising synthetic fibers (e.g. TYVEK®), collagen films, chitosan films, rayon, cellophane, and the like. Suitable webs further include laminates or blends of these materials. Suitable films include both cast and blown. Exemplary thermoplastic films suitable for use as the second substrate are low density polyethylene ("LDPE"), linear low-density polyethylene ("LLDPE"), and blends of LLDPE and LDPE. Films may be apertured.

Substrates can also optionally include colorants, such as pigment, lake, toner, dye, ink, or other agent used to impart a color to a material, to improve the visual appearance of a substrate or the resultant laminate. Suitable pigments herein include inorganic pigments, pearlescent pigments, interference pigments, and the like. Non-limiting examples of suitable pigments include talc, mica, magnesium carbonate, calcium carbonate, magnesium silicate, aluminum magnesium silicate, silica, titanium dioxide, zinc oxide, red iron oxide, yellow iron oxide, black iron oxide, carbon black, ultramarine, polyethylene powder, methacrylate powder, polystyrene powder, silk powder, crystalline cellulose, starch, titanated mica, iron oxide titanated mica, bismuth oxychloride, and the like. Suitable colored webs are described in US 2010/0233438 A1 and US 2010/0233439 A1.

Although the apparatuses and methods have been described in the context of the feminine hygiene article 5 shown in FIGS. 7-9, it is to be appreciated that the methods and apparatuses herein may be used to assemble and modify various substrates and/or elastic laminates that can be used with various process configurations and/or absorbent articles, such as for example, taped diapers or diaper pants.

Figure 10:
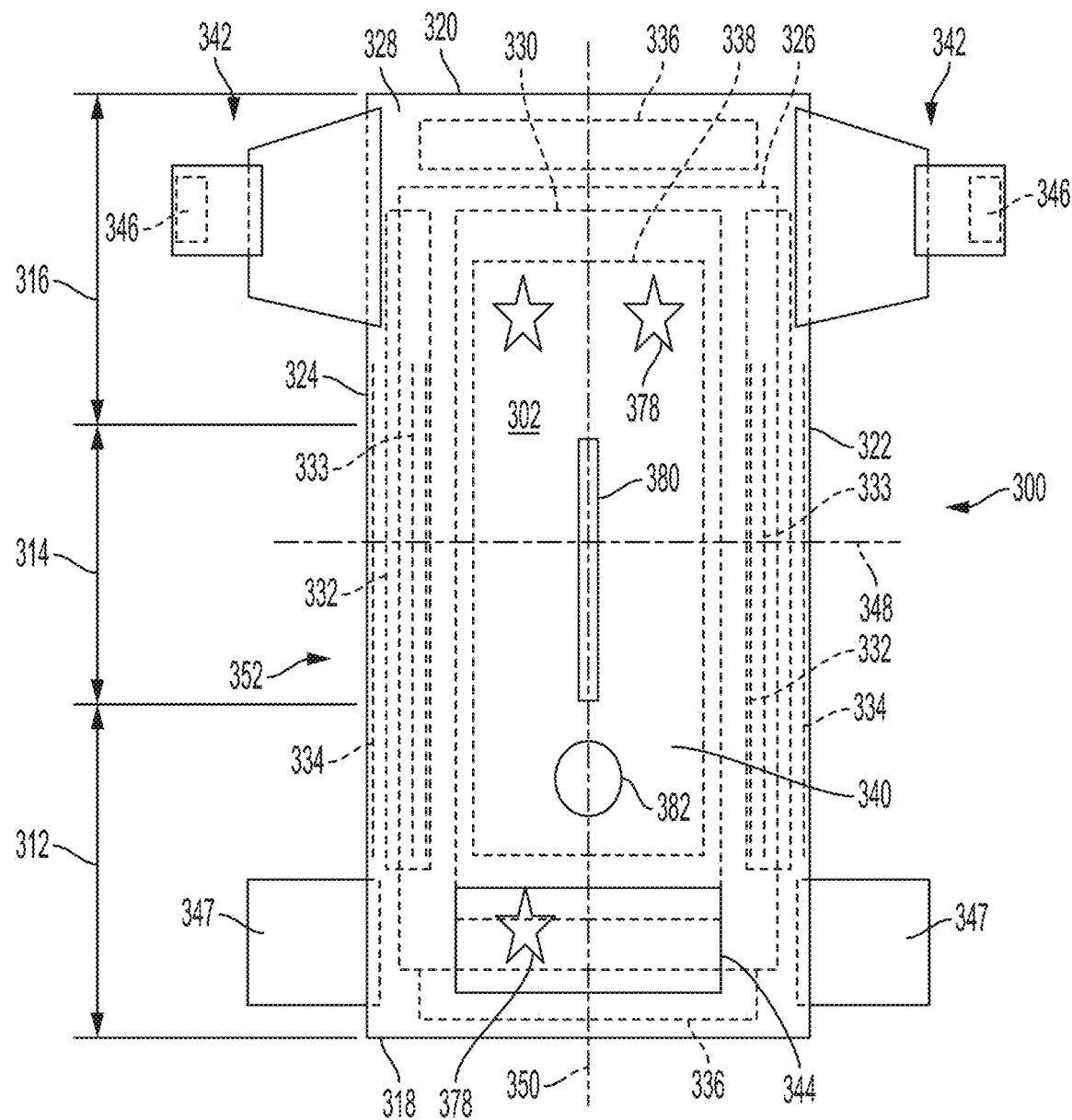
FIG. 10 is a plan view of an exemplary absorbent article in the form of a taped diaper, garment-facing surface facing the viewer, in a flat laid-out state.
Figure 11:
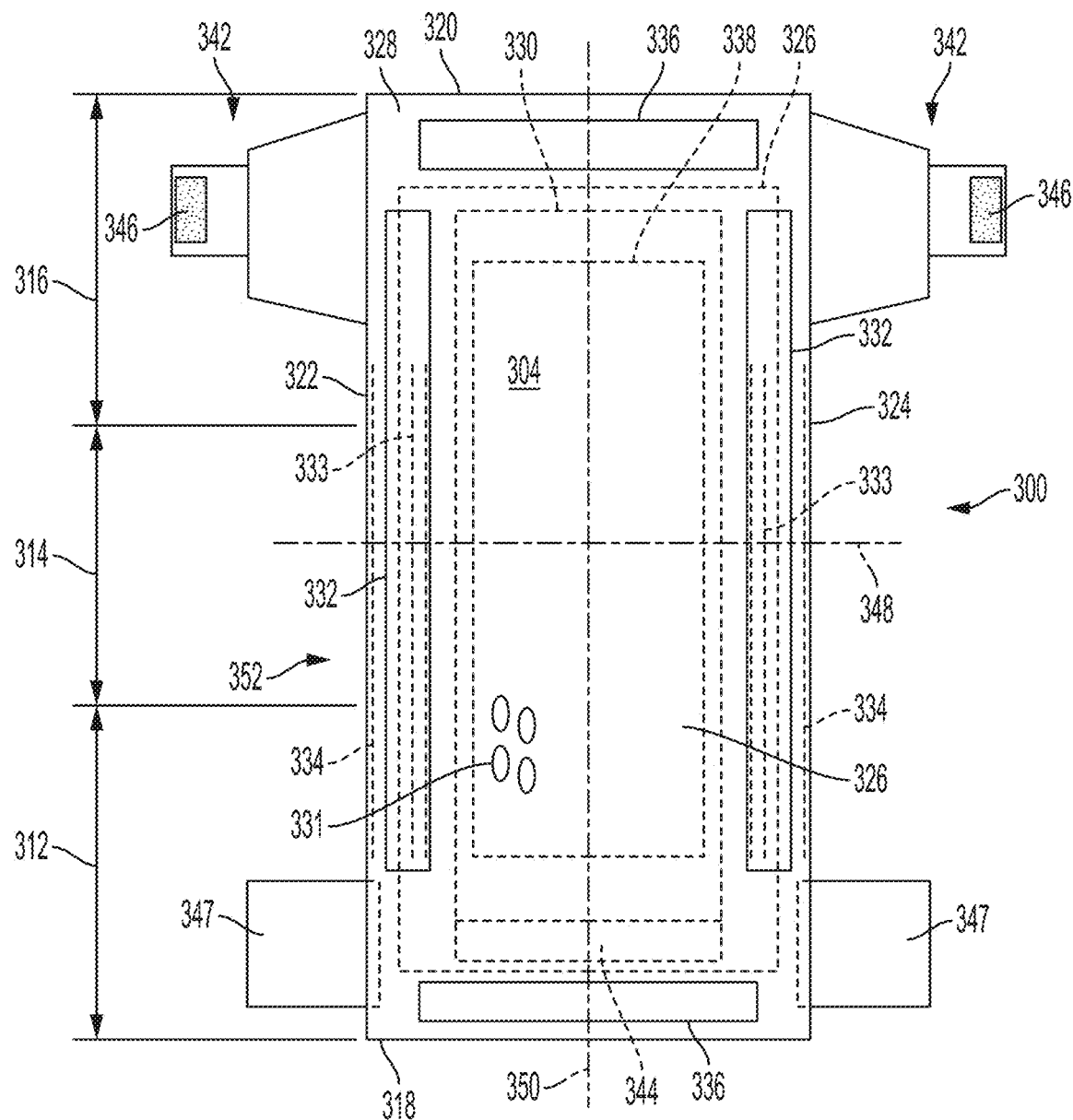
FIG. 11 is a plan view of the example absorbent article of FIG. 10, wearer-facing surface facing the viewer, in a flat laid-out state.
Figure 12:
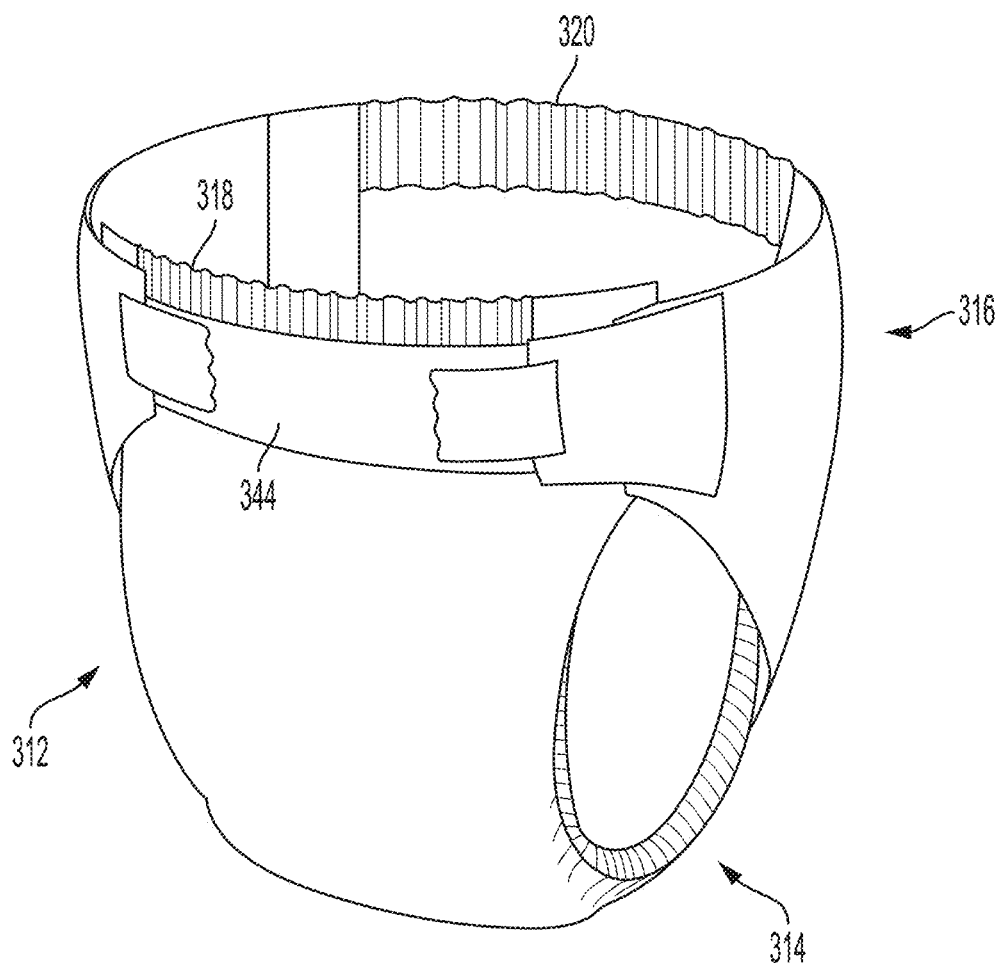
FIG. 12 is a front perspective view of the absorbent article of FIGS. 10 and 11 in a fastened position.

A taped diaper, is represented in FIGS. 10-12. FIG. 10 is a plan view of the example absorbent article 300, garment-facing surface 302 facing the viewer in a flat, laid-out state (i.e., no elastic contraction). The absorbent article 300 may comprise a front waist region 312, a crotch region 314, and a back waist region 316. The crotch region 314 may extend intermediate the front waist region 312 and the back waist region 316. The front waist region 312, the crotch region 314, and the back waist region 316 may each be ⅓ of the length of the absorbent article 300. The absorbent article may comprise a front end edge 318, a back end edge 320 opposite to the front end edge 318, and longitudinally extending, transversely opposed side edges 322 and 324 defined by the chassis 352.

The absorbent article may comprise a liquid permeable topsheet 326, a liquid impermeable backsheet 328, and an absorbent core 330 positioned at least partially intermediate the topsheet and the backsheet (see FIG. 11). The absorbent article may also comprise one or more pairs of barrier leg cuffs 332 with or without elastics 333, one or more pairs of leg elastics 334, one or more elastic waistbands 336, and/or one or more acquisition and/or distribution materials 338. The acquisition and/or distribution material or materials 338 may be positioned intermediate the topsheet 326 and the absorbent core 330. An outer cover material 340, such as a nonwoven material, may cover a garment-facing side of the backsheet 328. The absorbent article may comprise back ears 342 in the back waist region 316. The back ears 342 may comprise fasteners 346 and may extend from the back waist region 316 of the absorbent article 300 and attach (using the fasteners 346) to the landing zone area or landing zone material 344 on a garment-facing portion of the front waist region 312 of the absorbent article 300. The absorbent article 300 may also have front ears 347 in the front waist region 312. The absorbent article 300 may have a central lateral (or transverse) axis 348 and a central longitudinal axis 350. The central lateral axis 348 extends perpendicular to the central longitudinal axis 350.

Figure 13:
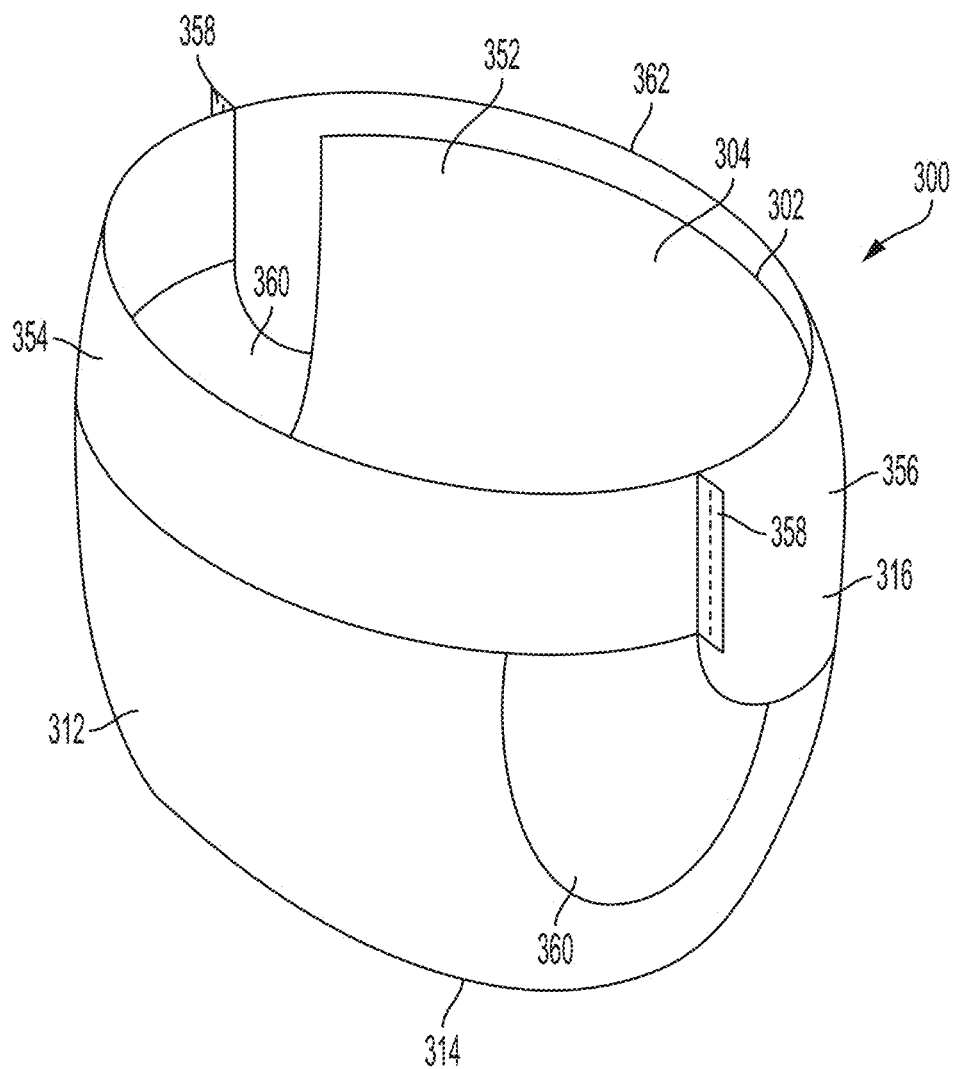
FIG. 13 is a front perspective view of an absorbent article in the form of a pant.
Figure 14:
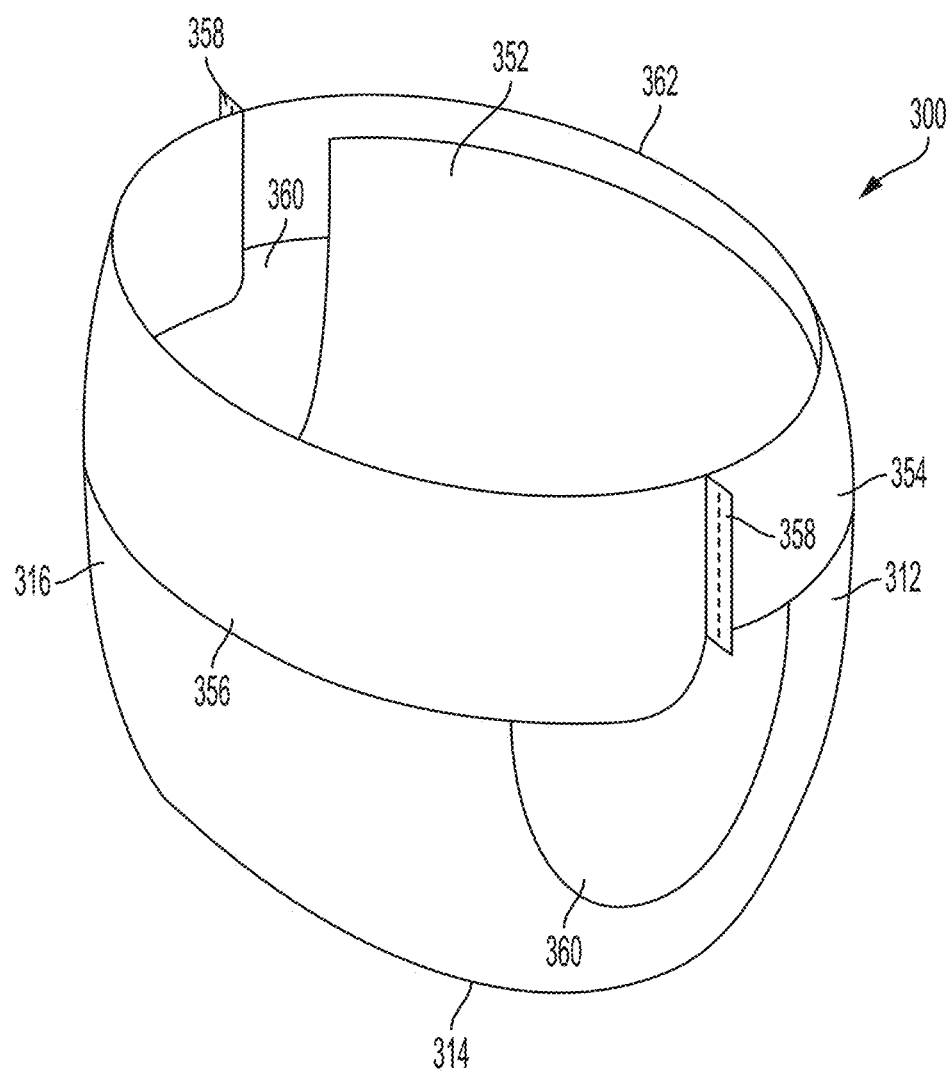
FIG. 14 is a rear perspective view of the absorbent article of FIG. 13.
Figure 15:
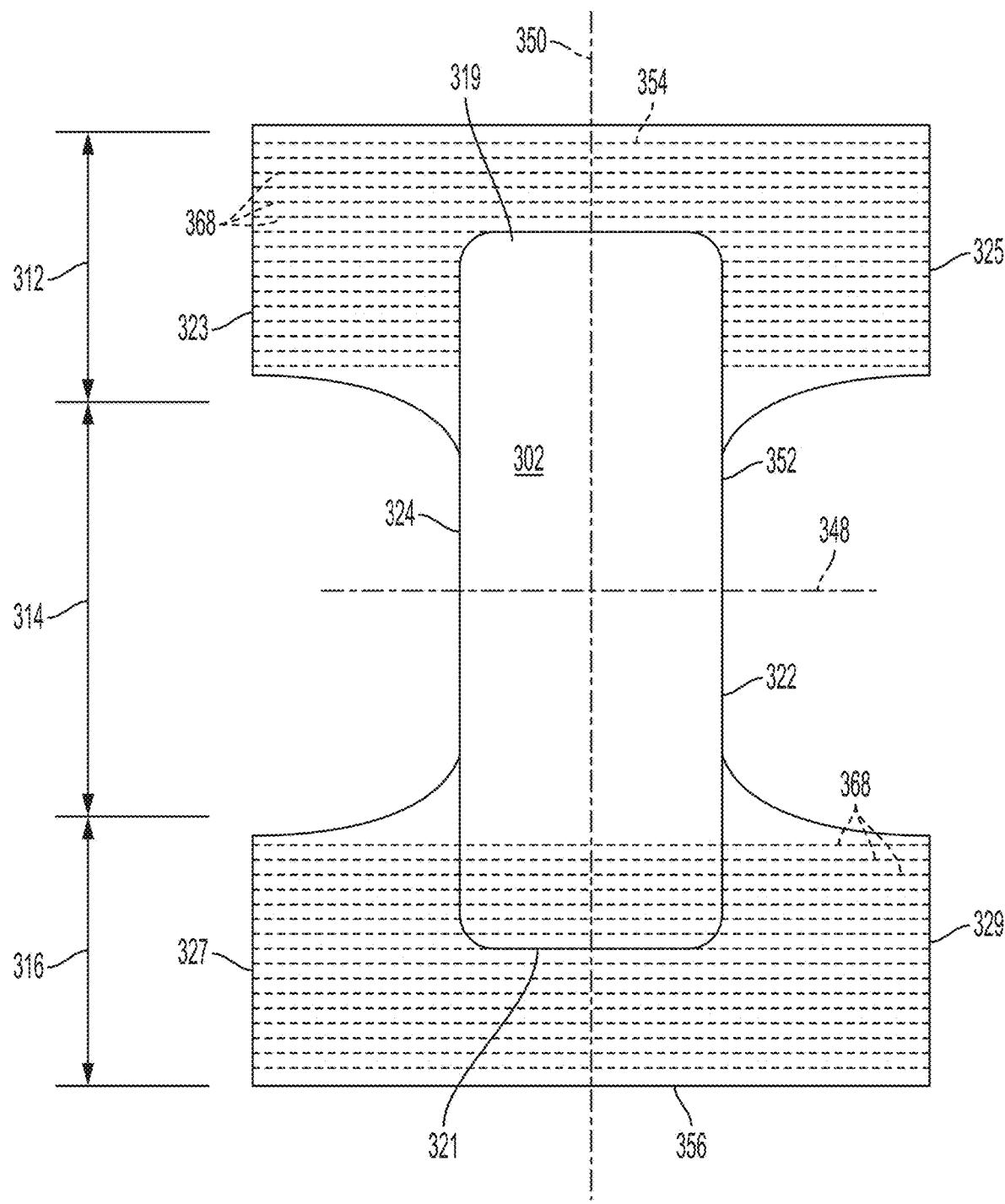
FIG. 15 is a plan view of the absorbent article of FIG. 13, laid flat, with a garment-facing surface facing the viewer.

In other instances, the absorbent article may be in the form of a pant having permanent or refastenable side seams. Suitable refastenable seams are disclosed in U.S. Pat. Appl. Pub. No. 2014/0005020 A1 and U.S. Pat. No. 9,421,137. Referring to FIGS. 13-15, an example absorbent article 300 in the form of a pant is illustrated. FIG. 13 is a front perspective view of the absorbent article 300. FIG. 14 is a rear perspective view of the absorbent article 300. FIG. 15 is a plan view of the absorbent article 300, laid flat, with the garment-facing surface facing the viewer. The absorbent article 300 may have a front waist region 312, a crotch region 314, and a back waist region 316. Each of the regions 312, 314, and 316 may be ⅓ of the length of the absorbent article 300. The absorbent article 300 may have a chassis 352 (sometimes referred to as a central chassis or central panel) comprising a topsheet 326, a backsheet 328, and an absorbent core 330 disposed at least partially intermediate the topsheet 326 and the backsheet 328, and an optional acquisition and/or distribution material 338, similar to that as described above with respect to FIGS. 10-12. The absorbent article may comprise a front belt 354 in the front waist region 312 and a back belt 356 in the back waist region 316. The front or back belt 354, 356 may be joined to a wearer-facing surface 304 or to a garment-facing surface 302 of chassis 352. Side edges 323 and 325 of the front belt 354 may be joined to side edges 327 and 329, respectively, of the back belt 356 to form two side seams 358. The side seams 358 may be any suitable seams known to those of skill in the art, such as butt seams or overlap seams, for example. When the side seams 358 are permanently formed or refastenably closed, the absorbent article 300 in the form of a pant has two leg openings 360 and a waist opening circumference 362. The side seams 358 may be permanently joined using adhesives or bonds, for example, or may be refastenably closed using hook and loop fasteners, for example.

The front and back belts 354 and 356 may comprise front and back inner belt layers and front and back outer belt layers having an elastomeric material (e.g., strands 368 or a film (which may be apertured)) disposed at least partially therebetween. The elastic elements or the film may be relaxed (including being cut) to reduce elastic strain over the absorbent core or, may alternatively, run continuously across the absorbent core. The elastics elements may have uniform or variable spacing therebetween in any portion of the belts. The elastic elements may also be pre-strained the same amount or different amounts. The front and/or back belts 354 and 356 may have one or more elastic element free zones where the chassis overlaps the belts 354, 356. In other instances, at least some of the elastic elements may extend continuously across the chassis 352.

The front and back inner belt layers and the front and back outer belt layers, may be joined using adhesives, heat bonds, pressure bonds or thermoplastic bonds. Various suitable belt layer configurations can be found in U.S. Pat. Appl. Pub. No. 2013/0211363 A1.

Front and back belt end edges may extend longitudinally beyond the front and back chassis end edges 319 and 321 (as shown in FIG. 15) or they may be coterminous. The front and back belt side edges may extend laterally beyond the chassis side edges 322 and 324. The front and back belts 354 and 356 may be continuous (i.e., having at least one layer that is continuous) from belt side edge to belt side edge. Alternatively, the front and back belts 354 and 356 may be discontinuous from belt side edge to belt side edge, such that they are discrete.

As disclosed in U.S. Pat. No. 7,901,393, the longitudinal length (along the central longitudinal axis 350) of the back belt 356 may be greater than the longitudinal length of the front belt 354, and this may be particularly useful for increased buttocks coverage when the back belt has a greater longitudinal length versus the front belt adjacent to or immediately adjacent to the side seams 358.

The front outer belt layer and the back outer belt layer may be separated from each other, such that the layers are discrete or, alternatively, these layers may be continuous, such that a layer runs continuously from the front belt end edge to the back belt end edge. This may also be true for the front and back inner belt layers—that is, they may also be longitudinally discrete or continuous. Further, the front and back outer belt layers may be longitudinally continuous while the front and back inner belt layers are longitudinally discrete, such that a gap is formed between them.

The front and back belts 354 and 356 may include slits, holes, and/or perforations providing increased breathability, softness, and a garment-like texture. Underwear-like appearance can be enhanced by substantially aligning the waist and leg edges at the side seams 358.

The front and back belts 354 and 356 may comprise graphics. The graphics may extend substantially around the entire circumference of the absorbent article 300 and may be disposed across side seams and/or across proximal front and back belt seams; or, alternatively, adjacent to the seams in the manner described in U.S. Pat. No. 9,498,389 to create a more underwear-like article. The graphics may also be discontinuous.

Alternatively, instead of attaching belts and to the chassis to form a pant, discrete side panels may be attached to side edges of the chassis. Suitable forms of pants comprising discrete side panels are disclosed in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

The topsheet 326 is the part of the absorbent article 300 that is in contact with the wearer's skin. The topsheet 326 may be joined to portions of the backsheet 328, the absorbent core 330, the barrier leg cuffs 332, and/or any other layers as is known to those of ordinary skill in the art. The topsheet 326 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (FIG. 11, element 331), may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Pub. No. US 2016/0136014 A1 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

The backsheet 328 is generally that portion of the absorbent article 300 positioned proximate to the garment-facing surface of the absorbent core 330. The backsheet 328 may be joined to portions of the topsheet 326, the outer cover material 340, the absorbent core 330, and/or any other layers of the absorbent article by any attachment methods known to those of skill in the art. The backsheet 328 prevents, or at least inhibits, the bodily exudates absorbed and contained in the absorbent core from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

The outer cover material (sometimes referred to as a backsheet nonwoven) 340 may comprise one or more nonwoven materials joined to the backsheet 328 and that covers the backsheet 328. The outer cover material 340 forms at least a portion of the garment-facing surface 302 of the absorbent article 300 and effectively "covers" the backsheet 328 so that film is not present on the garment-facing surface 302. The outer cover material 340 may comprise a bond pattern, apertures, and/or three-dimensional features.

As used herein, the term "absorbent core" 330 refers to the component of the absorbent article having the most absorbent capacity and that comprises an absorbent material. In some instances, absorbent material may be positioned within a core bag or a core wrap. The absorbent material may be profiled or not profiled, depending on the specific absorbent article. The absorbent core 330 may comprise, consist essentially of, or consist of, a core wrap, absorbent material, and glue enclosed within the core wrap. The absorbent material may comprise superabsorbent polymers, a mixture of superabsorbent polymers and air felt, only superabsorbent material, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may be free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 314 of the absorbent article 300.

The absorbent core 330 may have areas having little or no absorbent material, where a wearer-facing surface of the core bag may be joined to a garment-facing surface of the core bag. These areas having little or no absorbent material may be referred to as channels. These channels can embody any suitable shapes and any suitable number of channels may be provided. In other instances, the absorbent core may be embossed to create the impression of channels.

Referring to FIGS. 10 and 11, for example, the absorbent article 300 may comprise one or more pairs of barrier leg cuffs 332 and one or more pairs of leg elastics 334. The barrier leg cuffs 332 may be positioned laterally inboard of leg elastics 334. Each barrier leg cuff 332 may be formed by a piece of material which is bonded to the absorbent article 300 so it can extend upwards from a wearer-facing surface 304 of the absorbent article 300 and provide improved containment of body exudates approximately at the junction of the torso and legs of the wearer. The barrier leg cuffs 332 are delimited by a proximal edge joined directly or indirectly to the topsheet and/or the backsheet and a free terminal edge, which is intended to contact and form a seal with the wearer's skin. The barrier leg cuffs 332 may extend at least partially between the front end edge 318 and the back end edge 320 of the absorbent article 300 on opposite sides of the central longitudinal axis 350 and may be at least present in the crotch region 314. The barrier leg cuffs 332 may each comprise one or more elastics 333 (e.g., elastic strands or strips) near or at the free terminal edge. These elastics 333 cause the barrier leg cuffs 332 to help form a seal around the legs and torso of a wearer. The leg elastics 334 extend at least partially between the front end edge 318 and the back end edge 320. The leg elastics 334 essentially cause portions of the absorbent article 300 proximate to the chassis side edges 322, 324 to help form a seal around the legs of the wearer. The leg elastics 334 may extend at least within the crotch region 314.

Referring to FIGS. 10 and 11, the absorbent article 300 may comprise one or more elastic waistbands 336. The elastic waistbands 336 may be positioned on the garment-facing surface 302 or the wearer-facing surface 304. As an example, a first elastic waistband 336 may be present in the front waist region 312 near the front end edge 318 and a second elastic waistband 336 may be present in the back waist region 316 near the back end edge 320. The elastic waistbands 336 may aid in sealing the absorbent article 300 around a waist of a wearer and at least inhibiting bodily exudates from escaping the absorbent article 300 through the waist opening circumference. In some instances, an elastic waistband may fully surround the waist opening circumference of an absorbent article.

One or more acquisition and/or distribution materials 338 may be present at least partially intermediate the topsheet 326 and the absorbent core 330. The acquisition and/or distribution materials 338 are typically hydrophilic materials that provide significant wicking of bodily exudates. These materials may dewater the topsheet 326 and quickly move bodily exudates into the absorbent core 330. The acquisition and/or distribution materials 338 may comprise one or more nonwoven materials, foams, cellulosic materials, cross-linked cellulosic materials, air laid cellulosic nonwoven materials, spunlace materials, or combinations thereof, for example. In some instances, portions of the acquisition and/or distribution materials 338 may extend through portions of the topsheet 326, portions of the topsheet 326 may extend through portions of the acquisition and/or distribution materials 338, and/or the topsheet 326 may be nested with the acquisition and/or distribution materials 338. Typically, an acquisition and/or distribution material 338 may have a width and length that are smaller than the width and length of the topsheet 326. The acquisition and/or distribution material may be a secondary topsheet in the feminine pad context. The acquisition and/or distribution material may have one or more channels as described above with reference to the absorbent core 330 (including the embossed version). The channels in the acquisition and/or distribution material may align or not align with channels in the absorbent core 330. In an example, a first acquisition and/or distribution material may comprise a nonwoven material and as second acquisition and/or distribution material may comprise a cross-linked cellulosic material.

Referring to FIGS. 10 and 11, the absorbent article 300 may have a landing zone area 344 that is formed in a portion of the garment-facing surface 302 of the outer cover material 340. The landing zone area 344 may be in the back waist region 316 if the absorbent article fastens from front to back or may be in the front waist region 312 if the absorbent article fastens back to front. In some instances, the landing zone 344 may be or may comprise one or more discrete nonwoven materials that are attached to a portion of the outer cover material 340 in the front waist region 312 or the back waist region 316 depending upon whether the absorbent article fastens in the front or the back. In essence, the landing zone 344 is configured to receive the fasteners 346 and may comprise, for example, a plurality of loops configured to be engaged with, a plurality of hooks on the fasteners 346, or vice versa.

Referring to FIG. 10, the absorbent articles 300 of the present disclosure may comprise graphics 378 and/or wetness indicators 380 that are visible from the garment-facing surface 302. The graphics 378 may be printed on the landing zone 340, the backsheet 328, and/or at other locations. The wetness indicators 380 are typically applied to the absorbent core facing side of the backsheet 328, so that they can be contacted by bodily exudates within the absorbent core 330. In some instances, the wetness indicators 380 may form portions of the graphics 378. For example, a wetness indicator may appear or disappear and create/remove a character within some graphics. In other instances, the wetness indicators 380 may coordinate (e.g., same design, same pattern, same color) or not coordinate with the graphics 378.

Referring to FIGS. 10 and 11, as referenced above, the absorbent article 300 may have front and/or back ears 347, 342 in a taped diaper context. Only one set of ears may be required in most taped diapers. The single set of ears may comprise fasteners 346 configured to engage the landing zone or landing zone area 344. If two sets of ears are provided, in most instances, only one set of the ears may have fasteners 346, with the other set being free of fasteners. The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover material 340, the backsheet 328, and/or the topsheet 326) or may be discrete components attached to a chassis 352 of the absorbent article on a wearer-facing surface 304, on the garment-facing surface 302, or intermediate the two surfaces 304, 302.

Referring again to FIG. 10, the absorbent articles of the present disclosure may comprise a sensor system 382 for monitoring changes within the absorbent article. The sensor system 382 may be discrete from or integral with the absorbent article 300. The absorbent article may comprise sensors that can sense various aspects of the absorbent article associated with insults of bodily exudates such as urine and/or BM (e.g., the sensor system 382 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 382 may sense components of urine, such as ammonia or urea and/or byproducts resulting from reactions of these components with the absorbent article 300. The sensor system 382 may sense byproducts that are produced when urine mixes with other components of the absorbent article 300 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 382 may also sense changes in pH, pressure, odor, the presence of gas, blood, a chemical marker or a biological marker or combinations thereof. The sensor system 382 may have a component on or proximate to the absorbent article that transmits a signal to a receiver more distal from the absorbent article, such as an iPhone, for example. The receiver may output a result to communicate to the caregiver a condition of the absorbent article 300. In other instances, a receiver may not be provided, but instead the condition of the absorbent article 300 may be visually or audibly apparent from the sensor on the absorbent article.

Other materials that may be considered substrates, or include substrates as a part of a final product. Substrates may include films. Suitable films include water-soluble or water-dispersible films. The films may be thermo-formable and/or vacuum-formable. The film may include polymeric materials. Suitable polymeric materials include polyvinyl alcohols, hydroxypropyl methyl cellulose (HPMC), copolymers thereof, derivatives thereof, or combinations thereof. The film may further include one or more additive ingredients, such as plasticizer, surfactant, cleaning additives, water, or other suitable adjuncts. The films may be obtained by casting, blow-molding, extrusion or blown extrusion of the polymeric material, as known in the art. The film may have a thickness of from about 20 to 150 microns, or from about 50 to 110 microns. Suitable water-soluble films may include those supplied by MonoSol, LLC (Merrillville, Indiana, USA) under the trade references M8630, M8900, M8779, M9467, and M8310, as well as films, such as PVA films, having corresponding solubility, deformability, and/or sealing characteristics. Suitable films are also described in U.S. Pat. Nos. 6,166,117 and 6,787,512; U.S. Pat. Appl. Pub. Nos. 2006/0213801, 2011/0186468, and 2011/0188784; and WO 2010/119022.

The films may be formed, for example by thermoforming and/or vacuum-forming, into unitized dose pouches, such as single- or multi-compartment pouches. One or more films may be formed into a web of sealed compartments via a continuous or a discontinuous process, and the web may be cut to form individual pouches. The pouches may contain a composition, such as a fabric care or hard surface care composition. Such compositions may be in the form of liquid, gel, solid, granular, or combinations thereof. Suitable pouches and processes for making such pouches are described in WO 2002/042408 and WO 2009/098659. Commercially available pouches include those marketed as TIDE PODS, GAIN FLINGS, and CASCADE ACTIONPACS (each available from The Procter & Gamble Company, Cincinnati, Ohio, USA).

Further, substrates may be used in cleaning products. For example, a duster cleaning article may comprise a nonwoven sheet having tow fibers joined thereto. The cleaning article may have a longitudinal axis. The tow fibers may be joined to the nonwoven sheet in a generally transverse direction and particularly in a direction normal the longitudinal axis, to provide a laminate structure of two layers.

If desired, the cleaning article may comprise additional layers, also referred to herein as laminae. For example, the tow fibers may be disposed intermediate two nonwoven sheets. Plural laminae of tow fibers may be disposed intermediate the nonwoven sheets and/or outboard thereof. Optionally, one or more of the nonwoven sheets may be cut to comprise strips. The strips may be generally normal to the longitudinal axis.

The tow fibers and/or nonwoven sheets may comprise an additive to assist in removal of dust and other debris from the target surface. The additive may comprise wax, such as microcrystalline wax, oil, adhesive and combinations thereof. The cleaning article may be made according to U.S. Pat. No. 6,813,801 and according to commonly assigned U.S. Pat. Nos. 7,803,726; 8,756,746; 8,763,197 and 8,931,132.

The laminae of the cleaning article may be joined together using adhesive, thermal bonding, ultrasonic welding, etc. If desired, the bonding lines may be generally parallel to the longitudinal axis and may be continuous, or discontinuous as desired. Three longitudinally parallel bonding lines may be utilized to define two sleeves.

The two sleeves may accept one or more complementary fork tines of a handle. The fork tines may be removably inserted into the sleeves of the cleaning article to provide for improved ergonomics. The handle may be plastic and made according to the teachings of U.S. Pat. Nos. 7,219,386; 7,293,317, 7,383,602 and/or commonly assigned U.S. Pat. No. 8,578,564. Representative dusters are sold by the instant assignee under the name SWIFFER®.

Further still, substrates may include cleaning sheets. The cleaning sheet may comprise a nonwoven. The nonwoven may be synthetic and/or have cellulosic fibers therein. The synthetic fibers may comprise carded, staple, wet laid, air laid and/or spunbond fibers. The nonwoven cleaning sheet may be made according to a hydro-entangling process to provide a texture and a basis weight of about 20 to about 120 gsm.

Optionally, the cleaning sheet may further comprise an additive, to improve cleaning performance and/or enhance the cleaning experience. The additive may comprise wax, such as microcrystalline wax, oil, adhesive, perfume and combinations thereof. The cleaning sheet may be made according to commonly assigned U.S. Pat. Nos. 6,305,046; 6,484,346; 6,561,354; 6,645,604; 6,651,290; 6,777,064; 6,790,794; 6,797,357; 6,936,330; D409,343; D423,742; D489,537; D498,930; D499,887; D501,609; D511,251 and/or D615,378.

In some embodiments, the cleaning sheet may comprise layers, to provide for absorption and storage of cleaning fluid deposited on the target surface. If desired, the cleaning sheet may comprise absorbent gelling materials to increase the absorbent capacity. The absorbent gelling materials may be distributed within the cleaning sheet in such a manner to avoid rapid absorbency and absorb fluids slowly, to provide for the most effective use of the cleaning sheet.

The cleaning sheet may comprise multiple layers. The lowest, or downwardly facing outer layer, may comprise apertures to allow for absorption of cleaning solution therethrough and to promote the scrubbing of the target surface. Intermediate layers may provide for storage of the liquids and may comprise the absorbent gelling materials. The cleaning sheet may have an absorbent capacity of at least 10, 15, or 20 grams of cleaning solution per gram of dry cleaning sheet, as set forth in commonly assigned U.S. Pat. Nos. 6,003,191 and 6,601,261. The top or upwardly facing outer layer may be liquid impervious in order to minimize loss of absorbed fluids. The top layer may further provide for releasable attachment of the cleaning sheet to a cleaning implement. The top layer may be made of a polyolefinic film, such as LDPE.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus comprising:
   a tooling roll; and
   an anvil roll operably engaged with the tooling roll at a nip,
   wherein the tooling roll and the anvil roll are rotatable about respective axes of rotation, the axes of rotation and the nip being perpendicular to a machine direction and parallel with a cross direction,
   wherein the anvil roll comprises:
      an outer surface comprising a plurality of discrete engaging portions disposed thereabout, wherein the discrete engaging portions are radially inwardly displaceable with respect to the anvil roll axis of rotation, wherein the engaging portions have radially outermost surfaces and are configured to engage one or more features of the tooling roll in the nip, wherein each of the plurality of discrete engaging portions extend from a first side to a second side of the anvil roll in a direction substantially perpendicular to the machine direction to form a portion of the outer surface;
      a rigid portion positioned adjacent to at least two of the plurality of discrete engaging portions; and
      a plurality of discrete spring elements, wherein at least three spring elements of the plurality of discrete spring elements being in mechanical communication with each of the plurality of discrete engaging portions, wherein the at least three spring elements are each separated in the cross direction by a void and disposed radially beneath the outer surface, wherein the plurality of discrete spring elements are configured to flex and thereby provide for elastic radially inward displacement of the plurality of discrete engaging portions relative the rigid portion as the discrete engaging portions rotate through the nip, and thereby provide compliance, wherein two spring elements of the last three spring elements have different spring constants.

2. The apparatus of claim 1 wherein each of the discrete spring elements and its associated discrete engaging portion are integrally formed.

3. The apparatus of claim 1 wherein the discrete spring elements and the rigid portion are integrally formed.

4. The apparatus of claim 1 wherein the discrete spring elements, the engaging portions and the rigid portion are integrally formed.

* * * * *